(12) United States Patent
Cargill et al.

(10) Patent No.: US 6,963,399 B2
(45) Date of Patent: Nov. 8, 2005

(54) METHOD AND APPARATUS FOR QUANTIFYING AN "INTEGRATED INDEX" OF A MATERIAL MEDIUM

(76) Inventors: Robert L. Cargill, 1508 Pine Grove Way, San Jose, CA (US) 95129; Claudio I. Zanelli, 2100 Prospect St., Menlo Park, CA (US) 94025

( * ) Notice: Subject to any disclaimer, the term of this patent is extended or adjusted under 35 U.S.C. 154(b) by 291 days.

(21) Appl. No.: 10/274,330

(22) Filed: Oct. 18, 2002

(65) Prior Publication Data

US 2003/0095256 A1 May 22, 2003

Related U.S. Application Data

(60) Provisional application No. 60/346,915, filed on Oct. 18, 2001.

(51) Int. Cl.$^7$ ................................................. G01J 3/00
(52) U.S. Cl. ....................................... 356/328; 356/300
(58) Field of Search ................................ 356/300, 328; 250/330

(56) References Cited

U.S. PATENT DOCUMENTS

| | | | |
|---|---|---|---|
| 3,598,995 A | 8/1971 | Inoue | 250/71 R |
| 3,825,762 A | 7/1974 | White | 250/458 |
| 3,851,970 A | 12/1974 | Adler et al. | 356/51 |
| 4,015,130 A | * 3/1977 | Landry et al. | 356/310 |
| 4,176,957 A | * 12/1979 | Maeda et al. | 356/325 |
| 4,487,502 A | 12/1984 | Fantozzi et al. | 356/125 |
| 4,546,256 A | 10/1985 | Denisov et al. | 250/372 |
| 4,755,056 A | 7/1988 | Yasuda et al. | 356/51 |
| 4,952,027 A | 8/1990 | Saito et al. | 350/174 |
| 5,017,785 A | 5/1991 | Rasanen | 250/345 |
| 5,022,754 A | 6/1991 | Varnham | 356/300 |
| 5,040,889 A | 8/1991 | Keane | 356/51 |
| 5,126,569 A | 6/1992 | Carlson | 250/341 |
| 5,339,151 A | * 8/1994 | Shinn | 356/328 |
| 5,363,188 A | 11/1994 | Didelot et al. | 356/124.5 |
| 5,489,978 A | 2/1996 | Okumura et al. | 356/124 |
| 5,555,085 A | 9/1996 | Bogdanowicz et al. | 356/300 |
| 5,657,116 A | 8/1997 | Kohayakawa | 356/124 |
| 5,734,578 A | * 3/1998 | Oh | 356/303 |

(Continued)

OTHER PUBLICATIONS

The American Conference of Government Industrial Hygienists (ACGIH) 2001 Handbook of TLVs and BEIs (Threshold Limit Values and Biological Exposure Indices, pp. 151–158.

Australian Standard AS 1067.1–1990, "Sunglasses and Fashion.Spectacles, Part 1: Safety Requirements", Standards Association of Australia.

Australian/New Zealand AS / NZS 1338.1:1992, "Filters for Eye Protectors, Part 1 : Filters for protection against radiation generated in welding and allied operations", Standards Association of Australia.

(Continued)

Primary Examiner—Gregory J. Toatley, Jr.
Assistant Examiner—Kara Geisel
(74) Attorney, Agent, or Firm—Haverstock & Owens LLP

(57) ABSTRACT

An apparatus for and method of calculating an integrated index of a transparent, translucent or opaque material for a desired wavelength range, the method comprising measuring a filtered value of the material as a function of wavelength within the desired wavelength range and calculating a protection index from the measured filtered value. The integrated index is used to quantify the ultraviolet, infra-red, erythemal or aphakic exposure properties of the material. In addition, the integrated index is used to quantify the photopic and/or scotopic response capabilities of the material. Further, the integrated index is used to quantify the differential or mean color indices of the material in comparison to the color spectrum or another material. Moreover, the integrated index is used to quantify the heat flux absorbed by the material.

65 Claims, 11 Drawing Sheets

U.S. PATENT DOCUMENTS

| | | | |
|---|---|---|---|
| 5,949,535 A | 9/1999 | Hall | 356/124 |
| 5,971,537 A | 10/1999 | Fukuma et al. | 351/44 |
| 6,078,389 A | 6/2000 | Zetter | 356/300 |
| 6,094,275 A * | 7/2000 | Lin | 356/445 |
| 6,178,341 B1 | 1/2001 | Macfarlane et al. | 600/310 |
| 6,198,531 B1 | 3/2001 | Myrick et al. | 356/300 |
| 6,304,326 B1 | 10/2001 | Aspnes et al. | 356/369 |
| 6,333,500 B2 | 12/2001 | Gehring et al. | 250/341.1 |
| 6,335,792 B1 | 1/2002 | Tsuchiya | 356/432 |
| 6,359,684 B2 * | 3/2002 | Ikezawa et al. | 356/124 |
| 6,577,387 B2 * | 6/2003 | Ross et al. | 356/124 |
| 2001/0055112 A1 | 12/2001 | Matsubara | 356/300 |

OTHER PUBLICATIONS

Australian / New Zealand AS / NZS 1338.1:1992 "Filters for Eye Protectors, Part 2: Filters for protection against ultra-violet radiation", Standards Association of Australia.

Australian / New Zealand AS / NZS 1338.1:1992 "Filters for Eye Protectors, Part 3:Filters for protection against infra–red radiation", Standards Association of Australia.

"The Effects of Solar UV Radiation on the Eye", the United Nations Environment Programme, World Health Organization, 1994.

Pamphlet entitled "Sunglasses are More than Shades", the American Optometric Association.

* cited by examiner

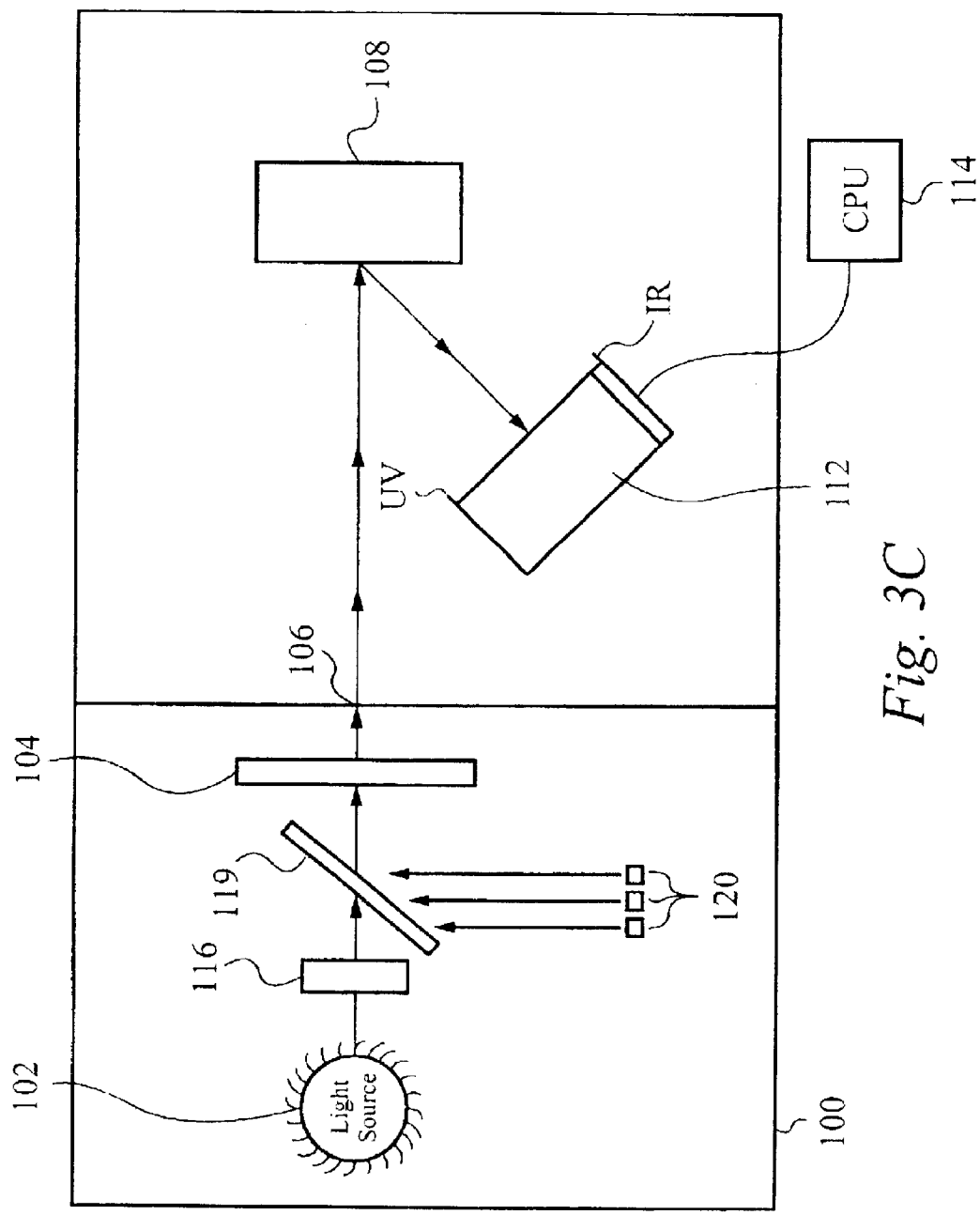

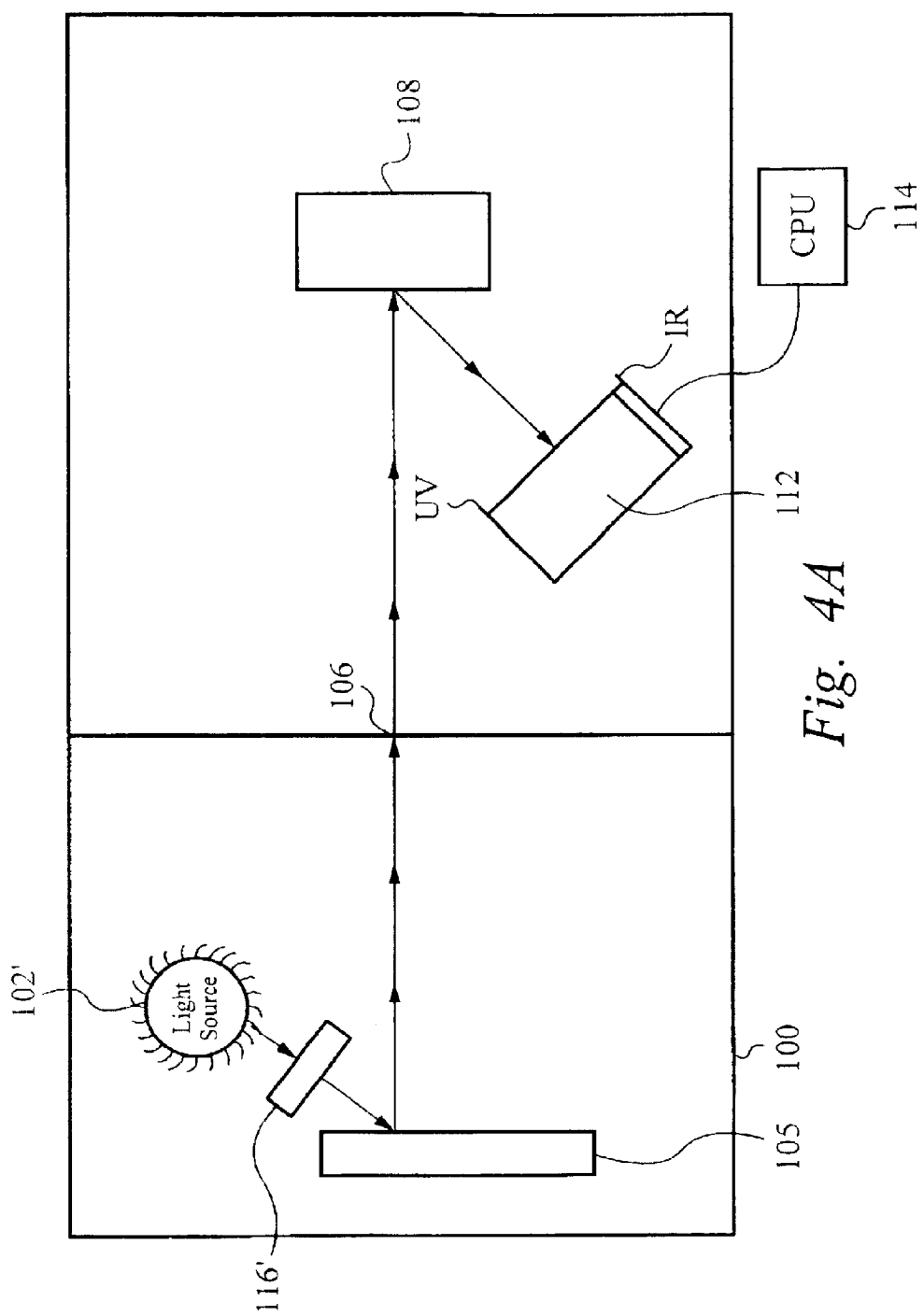

METHOD AND APPARATUS FOR QUANTIFYING AN "INTEGRATED INDEX" OF A MATERIAL MEDIUM

RELATED APPLICATION

This Patent Application claims priority under 35 U.S.C. 119 (e) of the co-pending U.S. Provisional Patent Application, Ser. No. 60/346,915 filed Oct. 18, 2001, and entitled "METHOD AND APPARATUS FOR QUANTIFYING AN INTEGRATED EXPOSURE INDEX". The Provisional Patent Application, Ser. No. 60/346,915 filed Oct. 18, 2001, and entitled "METHOD AND APPARATUS FOR QUANTIFYING AN INTEGRATED EXPOSURE INDEX" is also hereby incorporated by reference.

FIELD OF THE INVENTION

The invention relates to a method and apparatus for measuring optical properties in general, and specifically, to a method and apparatus for quantifying an integrated index of a material medium.

BACKGROUND OF THE INVENTION

A significant body of scientific evidence has shown that long-term ocular exposure to solar radiation is accompanied by specific detrimental physiological effects. Scientific studies have primarily considered two types of physiological effects: ocular effects (related to the eye) and erythemal effects (related to the skin). The statistical significance of these effects, including cataracts and other ocular damage mechanisms, correlates to increasing age and cumulative exposure to ambient sunlight. In a similar manner, the incidence of skin cancer and related cutaneous pathologies is also correlated to cumulative exposure to solar radiation. The aging population demographic in the industrialized nations and the decline in upper atmospheric ozone concentration have heightened the significance of this issue.

Leading scientific and regulatory organizations in several countries have conducted extensive investigations and have developed quantitative ocular radiation exposure guidelines. The intent of these standards is to provide a scientific basis for evaluating ocular exposure parameters and to assist in the control of health hazards. The technical basis of these standards is the fact that certain wavelengths within the solar radiation spectrum are more damaging than others. Ultraviolet (UV) and deep-blue wavelengths are prime examples of this effect. At a given intensity and time of exposure, the ultraviolet and blue wavelengths are more damaging to the human eye than other wavelengths in the visible band. For this reason, minimizing ocular exposure to UV radiation has long been an accepted principle in the occupational health sciences.

Generally, however, technical standards regarding the spectral transmission properties of commercial products such as eyewear and glazing materials have not been widely imposed by regulatory agencies or adhered to by manufacturers. A relevant example of this is the inaccurate claims of "100% UV protection" which persist throughout the retail stream of commerce for sunglasses. Currently, there is no widely accepted metric by which the safety attributes of such products can be accurately described.

Ambient solar radiation at the earth's surface is comprised of a broad electromagnetic spectrum, including ultraviolet, visible, and infrared wavelengths. Only the visible component of the sunlight can be perceived by the human eye. Classically, visible light is defined as electromagnetic radiation with wavelengths between approximately 400–700 nanometers (nm). The different visible wavelengths correspond to the various colors which are perceived by the human eye. The eye perceives purple and blue colors at the shorter-wavelength part of the visible spectrum (400–470 nm), and perceives red at the longer-wavelength part of the visible spectrum (660–700 nm). Green and yellow colors are perceived at the wavelengths in the middle of the visible spectrum. Visible wavelengths represent only a small fraction of the solar spectrum which penetrates the earth's atmosphere and reaches the surface of the planet. Ambient solar radiation at the Earth's surface includes a spectrum of wavelengths from approximately 300 nm (ultraviolet light) to infrared light at wavelengths exceeding 1000 nm.

Solar radiation with wavelengths below 300 nm is substantially absorbed in the upper atmosphere. This is fortunate since shorter-wavelength ultraviolet radiation is very damaging to organic matter. Without this atmospheric shielding effect, shorter-wavelength UV radiation would severely damage or extinguish many terrestrial life forms. Ultraviolet radiation with wavelengths between 185–280 nm is commonly called "UVC". This band of UV radiation is also called "germicidal UV" since it can quickly destroy pathogenic organisms even at moderate flux densities. Specialized UVC lamps are used in numerous anti-bacterial applications such as sterilization of potable water. Since the earth's atmosphere absorbs the shorter-wavelength UV radiation, exposure to UVC is normally associated with artificial lamp or laser sources which require special protective measures.

The commonly used terms "UVA" and "UVB" relate to ultraviolet radiation with wavelengths of 315–400 nm and 280–315 nm, respectively. Owing to shielding effects of our atmosphere, the UV component of solar radiation measured at the earth's surface occurs in a range of 300 to 400 nm in wavelength. High-quality eyewear should be designed to attenuate the UVA and UVB components of natural sunlight since these represent the elements of the ambient solar radiation spectrum which are most damaging to the human eye.

In the U.S., the American Conference of Governmental Industrial Hygienists (ACGIH) has conducted extensive studies of ocular radiation exposure issues. The research work conducted by the ACGIH has focused on technical criteria for evaluating exposure to a substantial range of substances and radiation types. In this regard, the ACGIH has published data supporting its Biological Exposure Indices (BEIs) and Threshold Limit Values (TLVs) as guidelines to assist in the control of health hazards. Threshold Limit Values (TLVs) relating to values for ocular exposure, include "spectral weighting functions" for specific wavelengths. In Europe, the International Committee on Illumination (CIE) in Paris has completed similar studies which have resulted in algorithms for calculating the "luminous transmittance" and "coloration factors" from spectrophotometric measurements of protective lenses.

This same methodology has been applied to infrared (IR) wavelengths. The ACGIH has developed spectral weighting functions and TLVs for "retinal thermal injury" from visible and IR wavelengths. Unlike UV radiation, the visible and IR wavelengths are more efficiently transmitted through the eye onto the retina. Historically, "glass blower's cataract" is a term used to describe the ocular damage which results from occupational exposure to the visible and IR radiation that is produced by high-temperature glass furnaces.

Although the specific ocular damage mechanism for visible and IR radiation differs from that of the UV wavelengths, the same principle holds true: the severity of the cumulative ocular damage effects varies as a function of wavelength and flux density or luminous intensity. In simple terms, certain wavelengths are more damaging than others at a given intensity. As shown in FIG. 1, the threshold exposure for ocular damage is dependent upon the wavelength of incident radiation.

For instance, the ACGIH "blue-light hazard function" (the spectral weighting function for retinal photochemical injury from chronic exposure to blue light) for light with a wavelength of 440 nm is 1000 times larger than for 590 nm wavelengths. In a similar manner, the ACGIH "relative spectral effectiveness" ($S_\lambda$) factor for ultraviolet light with a wavelength of 300 nm is 10,000 times higher than the S value at 400 nm. The standard Erythemal response curves, shown in FIG. 2, depict erythemal response or reddening of the skin to UV radiation, whereby UV radiation at a 300 nm wavelength has 25–100 times more erythemal potency than 315 nm radiation, as shown in FIG. 2.

The CIE concept of luminous transmittance is basically a mathematical model which embodies "photopic efficiency" and "relative energy" factors in order to quantify the total integrated brightness of ambient radiation, as perceived by a "standard observer" wearing lenses with a specific transmission spectrum. CIE luminous transmittance is calculated as the product of spectral transmittance ($T_\lambda$), photopic spectral luminous efficiency ($V_\lambda$), and the relative energy value of Standard Illuminant C ($S_\lambda$). The CIE has determined the values of $V_\lambda$ and $S_\lambda$ within the optical spectrum between 380–780 nm; the mathematical product of these two factors $[(V_\lambda)(S_\lambda)]$ is provided in the CIE standard at 10 nm intervals. Luminous transmittance is derived by first employing a conventional spectrophotometer to measure the transmission spectrum of the lens or substrate being characterized. The measured transmission values ($T_\lambda$) at 10 nm intervals are then multiplied by the respective values of $[(V_\lambda)(S_\lambda)]$. The mathematical products of these operations are then summed over the range of 380–780 nm and divided by 100,000 in order to derive the total (percent) luminous transmittance.

The CIE also promulgates a permutation of this model in the form of "coloration factors". Examples of these include the "Red Signal Visibility Factor" and the "Violet Factor". These variations of the CIE model apply the same basic calculation method to discrete portions of the spectrum. Respectively these are the red (620–780 nm) and violet (420–460 nm) parts of the visible spectrum. These "coloration factor" models are intended to address signal/sign visibility issues from the point of view of a "standardized" human observer.

In contrast to the present invention, however, the ACGIH work does not teach measured transmission spectra of protective lenses or other devices which attenuate an ambient radiation spectrum which has been characterized. The ACGIH document does not teach mathematical terms or reference factors of any kind which address the shielding or attenuation effects which are achieved by protective eyewear, fabrics, cosmetics, industrial applications and other transparent, translucent, or opaque optical materials which are designed to provide protection from ambient radiation. In addition, the CIE work does not teach the biological impact of the radiation spectrum. In addition, the CIE document contains no measurements or reference factors which address the ocular or erythemal effects of exposure to radiation spectra.

U.S. Pat. No. 5,949,535 to Hall teaches quantitatively rating protection values against solar radiation for eyewear. Hall further proposes that sunglass protection factors (SPFs), eye protection ratings (EPRs) and eye protection factors (EPFs) can be derived from the light transmission values of the sunglass lenses. Hall teaches that these factors are based on the average value of light transmission across a range of wavelengths, (280–400 nm for UV and 400–500 nm for blue light). These average transmission values are then converted to a linear (0–100) scale which yields a single numerical value for the measured property.

However, as shown in FIGS. 1 and 2 herein, the values of the Threshold Radiant Exposure and Relative Effectiveness are not linear as a function of wavelength. Instead, the light transmission values in the wavelength ranges of UV and blue light transmission, as shown in FIGS. 1 and 2 herein, are exponential or sinusoidal in nature. Hall does not take the non-linear effects of the light transmission values into account, but instead assumes that the exponential increase in source intensity as a function of wavelength is offset by an exponential decrease in toxicity of the longer wavelengths and further teaches that the net ocular damage is constant over the UV and blue wavelength bands (280–400 nm and 400–500 nm, respectively).

Therefore, Hall does not fully consider the significant variations in ambient solar irradiance, lens transmission, and physiological effectivity as functions of wavelength. In addition, Hall does not consider the physiological effects of infra-red wavelengths, the integrated physiological effects of the ambient solar spectrum, including UV, blue, and infra-red wavelengths, and the intensity and spectral distribution of the ambient illumination.

U.S. Pat. No. 5,971,537 to Fukuma, et.al (hereinafter Fukuma) teaches that the refractive properties of eyeglass lenses can be measured by an optical/electronic "lens specifying apparatus" which can also be used to measure spectral transmission properties in the UV and visible wavelengths. Fukuma further teaches that the invention can be used to measure and display the spatial distribution of these properties at different locations on the lens in order to characterize the properties of a "progressive" lens by mapping its refractive and spectral transmission properties at a plurality of points on the lens. However, Fukuma does not teach conducting and analyzing spectrophotometric measurements of eyeglass lenses in order to calculate indices which accurately characterize the physiological effects of transmitted radiation. In addition, Fukuma does not discuss transmission properties in relation to analyzing or rating the physiological impact of spectral transmission values of the lenses or optical substrates.

What is needed is a method of quantitative analysis of the total ocular and erythemal hazard of transparent or translucent materials. What is needed is a method of deriving and applying a quantitative index which defines the amount of ocular or erythemal hazard that is protected by the measured material properties of an intervening medium.

SUMMARY OF THE INVENTION

In one aspect of the invention, a method of calculating an integrated exposure index of a transparent or translucent material for a desired wavelength range. The method comprises measuring a modified, filtered value of the material as a function of wavelength within the desired wavelength range and calculating a protection index from the measured filtered value. The filtered value is measured by transmitting light within the desired wavelength range through the material. Alternatively, the filtered value is measured by reflecting light within the desired wavelength range off the material.

The method calculates the protection index by summing a calculated denominator coefficient for each incremental wavelength within the desired wavelength range. Each denominator coefficient is calculated by combining an appropriate ambient spectral irradiance value with an appropriate hazard factor. In addition, the method further comprises summing a numerator coefficient for each wavelength within the desired wavelength range. The numerator coefficient is calculated by combining the appropriate ambient spectral irradiance value and the measured filtered value with the appropriate hazard factor. The method further comprises dividing the summed numerator coefficient by the summed denominator coefficient. The method further comprises subtracting the divided value from a whole value, thereby generating a protection value. The method further comprises multiplying the protection value by a value of 100.

Alternatively, the protection index is a heat flux index, whereby the heat flux index utilizes the hazard factor as an energy absorption factor within the wavelength range. The wavelength range has a minimum wavelength of 300 nanometers and a maximum wavelength within a maximum range of 1000 nanometers and 12000 nanometers. Alternatively, the protection index is an ocular protection index utilizing the hazard factor as a summation of a blue light hazard factor and a retinal thermal hazard factor for each wavelength within the wavelength range. The alternative the wavelength range having a minimum wavelength within a minimum range of 300 nanometers and 320 nanometers and a maximum wavelength within a maximum range of 900 nanometers and 1400 nanometers. Alternatively, the protection index is a UV protection index utilizing the hazard factor as a blue light hazard factor within the wavelength range. The wavelength range has a minimum wavelength within a minimum range of 180 nanometers and 320 nanometers and a maximum wavelength of 500 nanometers.

The protection index alternatively is a infra-red protection index utilizing the hazard factor as a retinal thermal factor within the wavelength range. The alternative wavelength range has a minimum wavelength within a minimum range of 300 nanometers and 770 nanometers and a maximum range of 900 nanometers and 1400 nanometers. Alternatively, the protection index is an aphakic protection index utilizing the hazard factor as an aphakic hazard factor within the wavelength range. The wavelength range having a minimum wavelength within a minimum range of 750 nanometers and 770 nanometers and a maximum wavelength within a maximum range of 900 nanometers and 1400 nanometers. Alternatively, the protection index is an erythemal protection index utilizing the hazard factor as an erythemal response factor within the wavelength range. The wavelength range has a minimum wavelength of 180 nanometers and a maximum wavelength within a maximum range of 320 nanometers and 400 nanometers.

Another method of quantifying a value representative of a responsiveness of a transparent, translucent or opaque material for a desired wavelength range comprises measuring a filtered value that is transmitted through or reflected off the material as a function of wavelength within the desired wavelength range and calculating an integrated response index from the measured filtered values. The integrated response index is calculated by summing a calculated denominator coefficient for each incremental wavelength within the desired wavelength range. Each denominator coefficient is calculated by combining a response function with an appropriate illumination source irradiance value. In addition, the index is calculated by summing a calculated a numerator coefficient for each wavelength within the desired wavelength range. The numerator coefficient is calculated by combining the appropriate illumination source irradiance value and the response function with the measured filtered value and dividing the numerator coefficient with the denominator coefficient.

Alternatively, the integrated response index is an integrated photopic response index utilizing the response function as an ocular photopic response function for each wavelength in the wavelength range. Alternatively, the integrated response index is an integrated scotopic response index utilizing the response function as an ocular scotopic response function for each wavelength in the wavelength range. Alternatively, the integrated response index is an integrated photopic-scotopic response index utilizing the response function as a summation of an ocular scotopic response function and an ocular photopic response function for each wavelength in the wavelength range. The wavelength range for each has a minimum wavelength of 400 nanometers, and the wavelength range having a maximum wavelength within a maximum range of 700 nanometers and 770 nanometers.

In another embodiment, a method of calculating an integrated index of a transparent, translucent or opaque material medium within a desired wavelength range. The method comprises measuring a first spectrum value for each wavelength within the desired wavelength range. The method comprises measuring a second spectrum value for each wavelength within the desired wavelength range. The method comprises calculating a differential color index from the measured first spectrum value and the measured second spectrum value.

The differential color index is calculated by summing a calculated denominator coefficient for each incremental wavelength within the desired wavelength range. Each denominator coefficient is calculated by combining a illumination source irradiance value with an ocular photopic index factor and the measured second spectrum value. In addition, the differential color index is calculated by summing a calculated a numerator coefficient for each wavelength within the desired wavelength range. The numerator coefficient is calculated by combining the illumination source irradiance value with the ocular photopic index factor and a difference between the measured first and second spectrum values. In addition, the differential color index is calculated by dividing the summed numerator coefficient by the summed denominator coefficient.

Alternatively, the wavelength range for the differential color index of a blue wavelength band includes a minimum wavelength of 400 nanometers and a maximum wavelength of 520 nanometers. Alternatively, the wavelength range for the differential color index of a red wavelength band includes a minimum wavelength of 620 nanometers and a maximum wavelength of 700 nanometers. Alternatively, the wavelength range for the differential color index of a yellow wavelength band includes a minimum wavelength of 520 nanometers and a maximum wavelength of 620 nanometers.

Another method of calculating an integrated index of a transparent, translucent or opaque material within a desired wavelength range comprises measuring a spectrum value of the material for each wavelength within the desired wavelength range and calculating a mean color index from the measured spectrum value. The mean color index is calculated by summing a plurality of numerator coefficients for each wavelength over the desired wavelength range. Each numerator coefficient combines the measured spectrum value with an illumination source irradiance value. In addition mean color index is calculated by summing a plurality of illumination source irradiance values for each wavelength within the desired wavelength range and dividing the summed numerator coefficients by the summed illumination source irradiance values. The mean color index is calculated over a wavelength having a minimum wavelength value in the wavelength range is 400 nanometers and a maximum wavelength value in the wavelength range has a maximum range between 750 nanometers and 770 nanometers.

An apparatus for calculating an integrated index value for a transparent, translucent or opaque material. The apparatus comprises a light source for emitting light within a desired wavelength through the material, wherein the material passes a modified light. The apparatus further includes a slit aperture positioned such that the modified light passing through the material passes through the slit aperture. The apparatus further includes a diffraction grating positioned such that modified light passing from the slit aperture reflects off the diffraction grating at a predetermined angle. The apparatus further includes a variable neutral density spatial filter coupled to a charge coupled device (CCD) array detector.

The spatial filter is configured to receive the modified light reflected from the diffraction grating. The spatial filter attenuates the spectrum detected by the charge coupled array detector in such a manner as to strongly attenuate wavelengths with higher signal strength and to allow other wavelengths to pass unattenuated. The apparatus further includes a controller coupled to the charge coupled array detector. The controller calculates the integrated index value of the material by comparing characteristics the modified spectrum with a reference spectrum within the desired wavelength.

In another aspect, an apparatus for calculating an integrated index value for a transparent, translucent or opaque material. The apparatus further includes means for emitting light within a desired wavelength through the material, wherein the light passing through the material is a modified light. The apparatus further includes means for diffracting the modified light at a predetermined angle. The apparatus further includes means for producing a spectrum, wherein the spectrum producing means is configured to receive the modified light. The apparatus further includes means for calculating the integrated index. The calculating means is coupled to the spectrum producing means, wherein the calculating means determines the integrated index value of the material by comparing characteristics the modified spectrum with a reference spectrum within the desired wavelength.

In yet another aspect, an apparatus for calculating an integrated index value for a material. The apparatus further includes a light source for emitting light within a desired wavelength at the material. The light is transmitted through or reflected off of the material, thereby producing a filtered, modified light. The apparatus further includes a grating for reflecting the modified light at a predetermined angle. The apparatus further includes a detector assembly for producing a spectrum from the modified light, wherein the detector assembly receives the modified light. The apparatus further includes a circuit for calculating the integrated index. The circuit is coupled to the detector assembly, wherein the circuit determines the integrated index value of the material by comparing characteristics the modified spectrum with a reference spectrum within the desired wavelength. The apparatus further comprises a solid state diode array detector that is coupled to the circuit. The variable neutral density spatial filter is a spatial filter.

The signals from the CCD array detector or photodiode array are digitized and stored in memory devices which form a part of the electronics assembly of the apparatus. The apparatus further includes a conditioning apparatus for conditioning the light into the desired wavelengths, whereby the conditioning apparatus is a color balance filter, a dichroic mirror or an integrating sphere. The light source further comprises a lamp and a plurality of light emitting diodes.

BRIEF DESCRIPTION OF THE DRAWINGS

FIG. 3C illustrates a schematic of an alternative spectrophotometer for a transmission application in accordance with the present invention.

FIG. 4A illustrates a schematic of an alternative spectrophotometer for a reflective application in accordance with the present invention.

DETAILED DESCRIPTION OF THE PRESENT INVENTION

Figure 1:
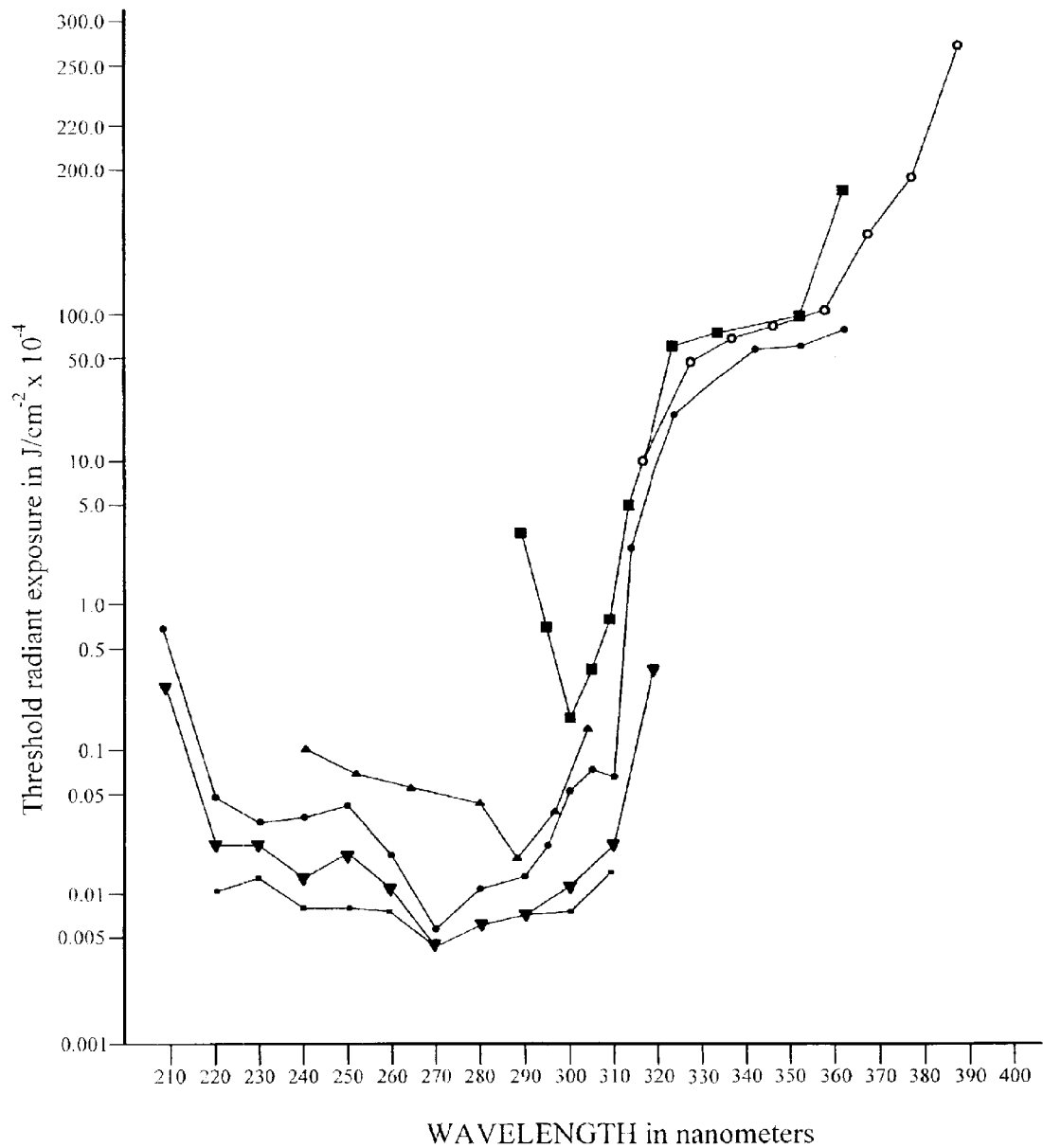
FIG. 1 illustrates a known relationship between the threshold radiant exposure as a function of wavelength for corneal and lens reactions.
Figure 2:
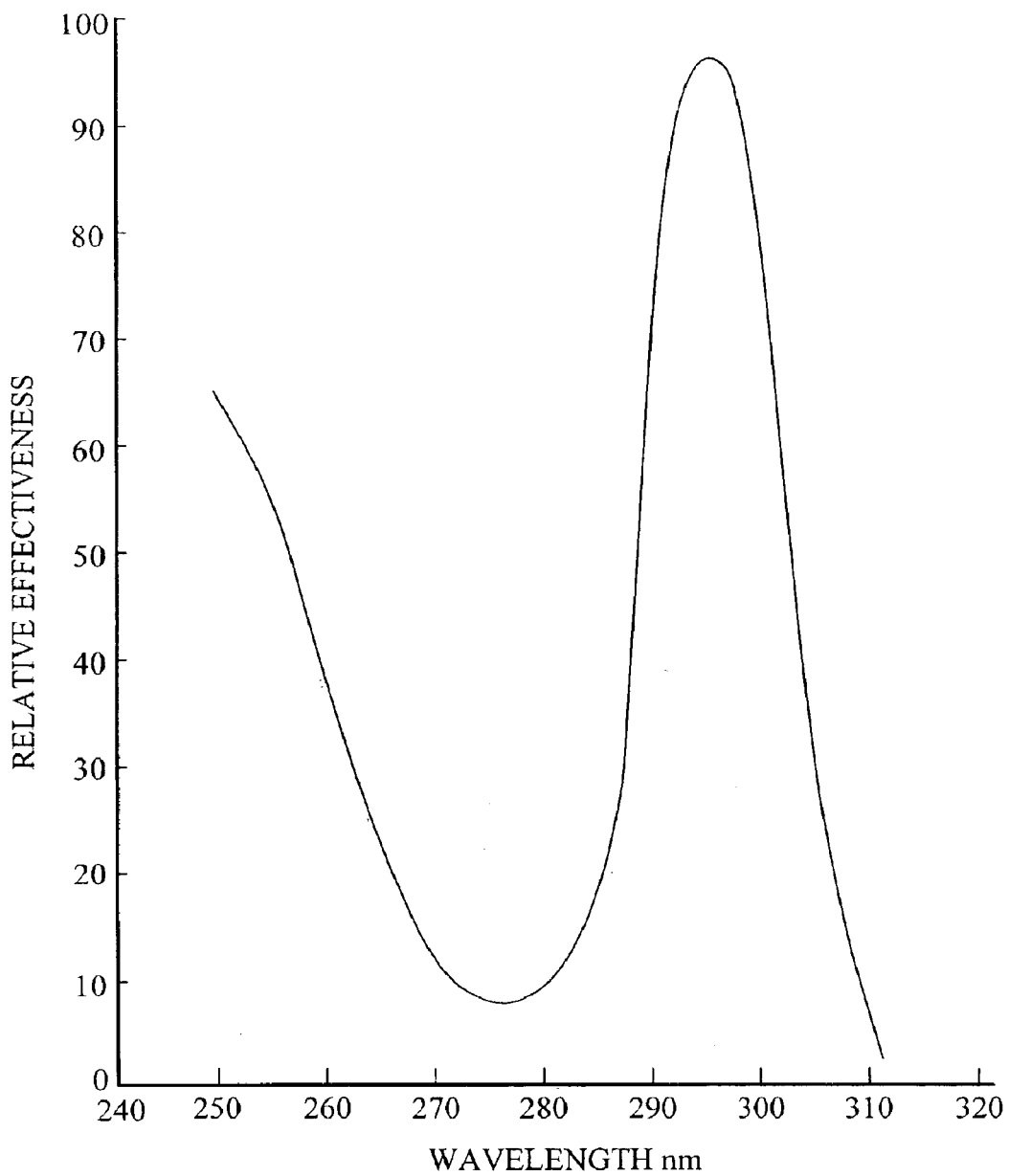
FIG. 2 illustrates a known relationship between the relative effectiveness as a function of wavelength for erythemal reactions.

In general, the present invention is directed to a system for quantitatively characterizing the biological significance of the total optical transmission spectrum of material mediums and products (hereinafter referred to as "products" for simplicity) which relate to human health issues. Products include transparent and translucent materials such as optical lenses, films, coatings and substrates including, but not limited to, sunglass lenses, regular eyeglass lenses, prescription eyeglass lenses, reading eyeglass lenses, sport goggles, scuba goggles, windows, coated windows, adhesive film appliques for windows and optical instrument components. In addition, such optical materials include applications in industrial safety products, including but not limited to, glazing materials, optical filters, industrial safety screens, welding safety filters and welding safety screens. Further, as used herein, products also include opaque materials such as optical coatings and other materials, including, but not limited to paints, cosmetics, fabrics and lotions.

The present invention utilizes optical transmission and reflection measurements of a product's material medium and employs computational algorithms which embody specific mathematical terms which correspond to the attenuation of incident radiation on the product material being characterized. The spectrophotometric measurements of optical spectra transmitted or reflected by the product's material medium are combined with wavelength-specific spectral weighting functions in order to calculate an "integrated index" for the material of the product being measured. The integrated index provides a quantitative measure of the total biological significance of the integrated, as-measured optical spectrum of the material medium of the product. In addition, specific integrated indices for various types of ocular as well as erythemal exposures are also discussed below.

The present invention utilizes an integrating spectrophotometer to measure the appropriate values and utilize these values to calculate the integrated index. The spectrophotometer of the present invention is of a size to fit on a table counter. Alternatively, the spectrophotometer of the present invention is a portable size, such as a spectrophotometer gun, which the user may carry. A schematic diagram of the preferred embodiment of the integrating spectrophotometer apparatus of the present invention is shown in the FIG. 3A. The spectrophotometer 100, shown in FIG. 3A, preferably contains a light source 102, a filtering device, such as a color balance filter 116, a removable substrate or material 104, such as an eyeglass lens, a slit aperture 106, a diffraction grating 108, a solid state diode array detector 112, such as a charge coupled device (CCD) array detector and a computer processor (CPU) 114 coupled to the solid state device array detector 112. Alternatively, the solid state diode array detector 112 is a photodiode array (not shown) instead of the CCD array detector. The light source 102 is preferably a halogen lamp, but may include any combination of one or more light sources, including, but not limited to halogen lamps, light emitting diodes (LEDs), xenon lamps and flourescent lamps, individually or in combination.

The color balance filter 116 (FIGS. 3A, 3C, 4A, 4C and 4D) in the spectrophotometer 100 of the present invention is preferably used to filter the light emitted from the light source 102, such that the filtered light passed to the material medium includes the wavelengths in the desired spectral intensity distribution. Alternatively, as shown in FIGS. 3B and 4B, the spectrophotometer 100 includes a variable neutral density spatial filter or spatial filter 110 which performs similar functions as the color balance filter 116, whereby the spatial filter 110 is coupled to the solid state diode array detector 112. It should be understood that the illustrated configurations in FIGS. 3A–3C and 4A–4D are exemplary. In any of these configurations, either the spatial filter 110 or the color balance filter 116 can be used. The color balance filter 116 is used in the preferred embodiment.

Figure 3A:
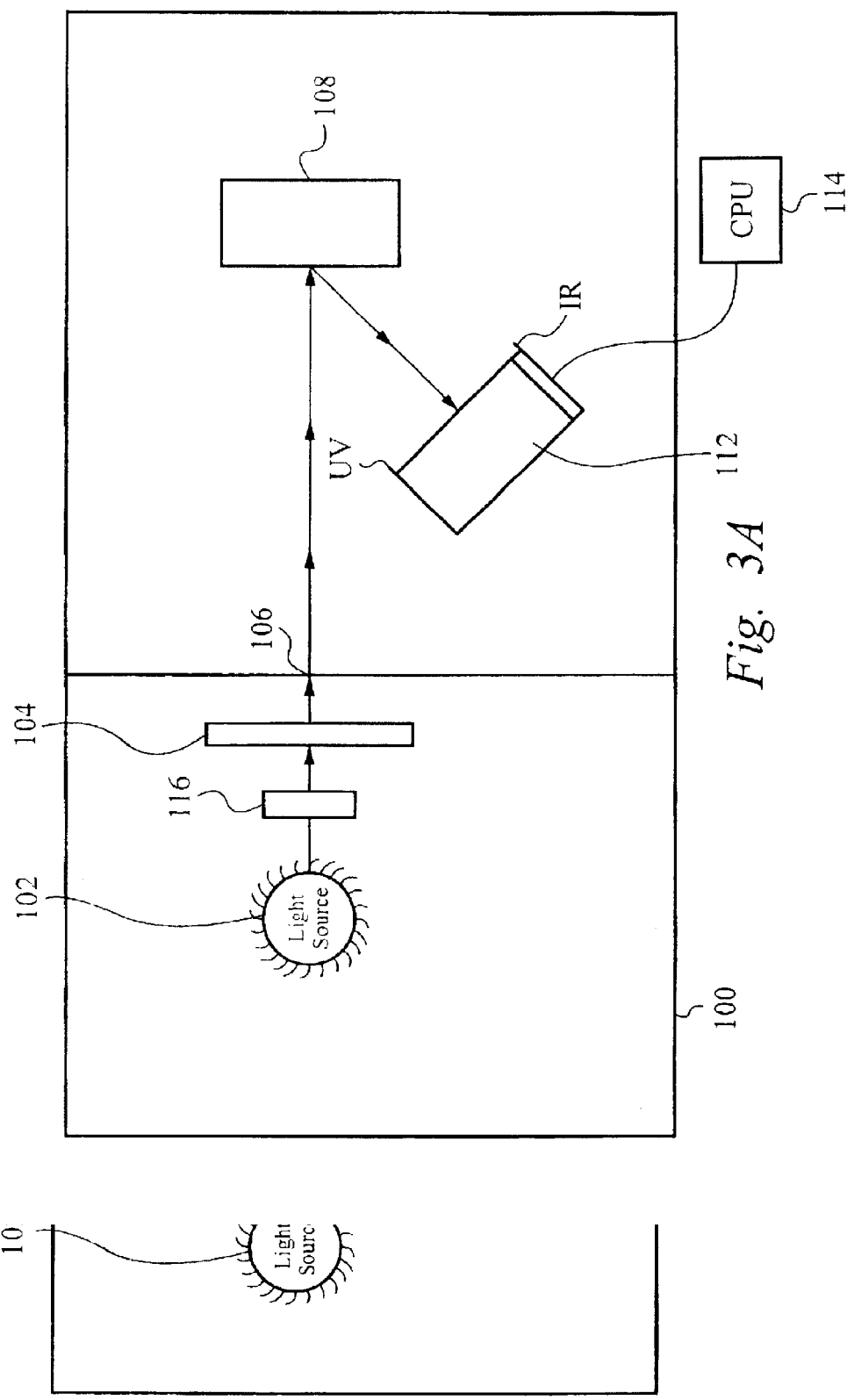
FIG. 3A illustrates a schematic of a preferred spectrophotometer for a transmission application in accordance with the present invention.
Figure 3B:
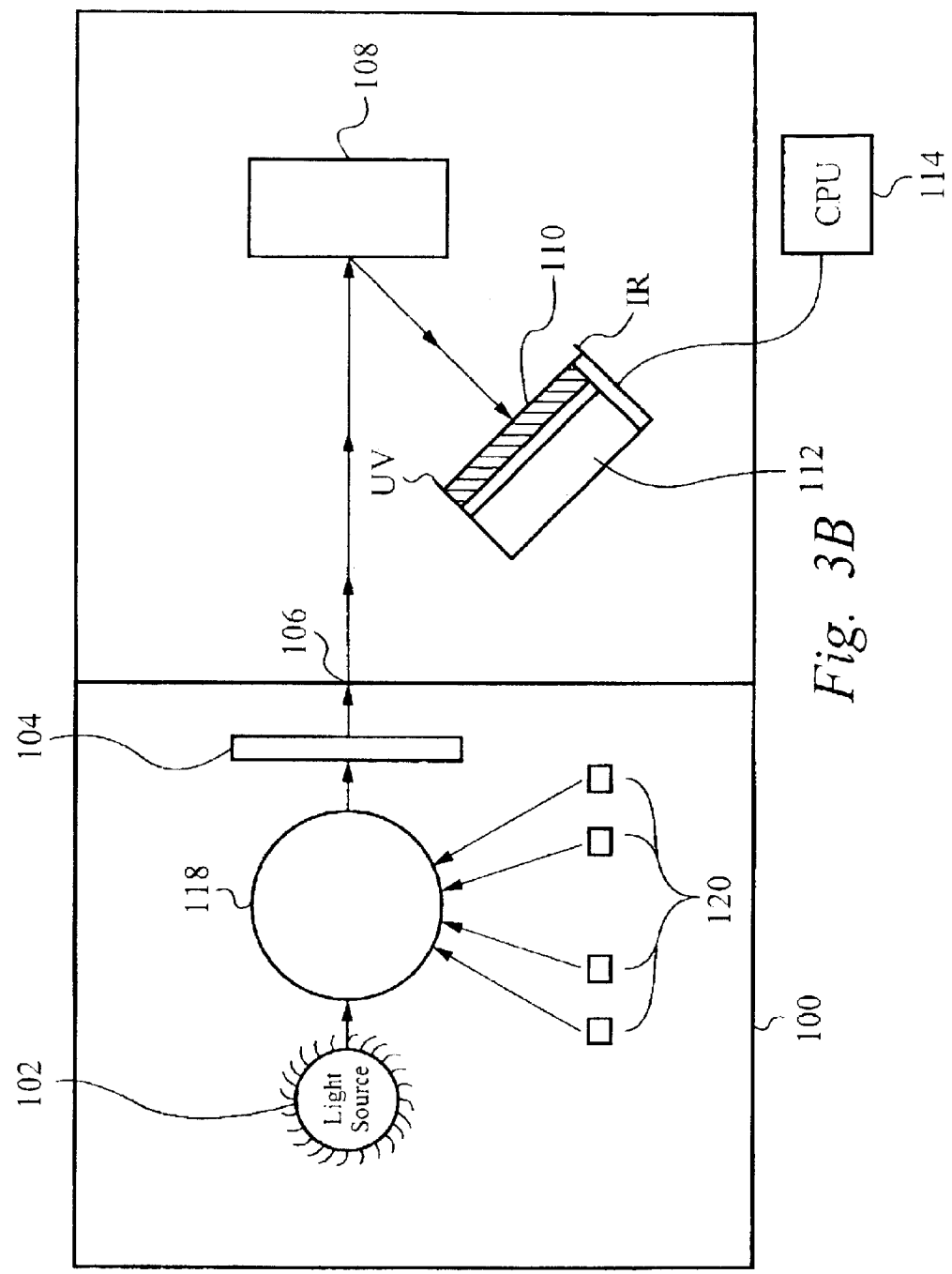
FIG. 3B illustrates a schematic of an alternative spectrophotometer for a transmission application in accordance with the present invention.
Figure 4B:
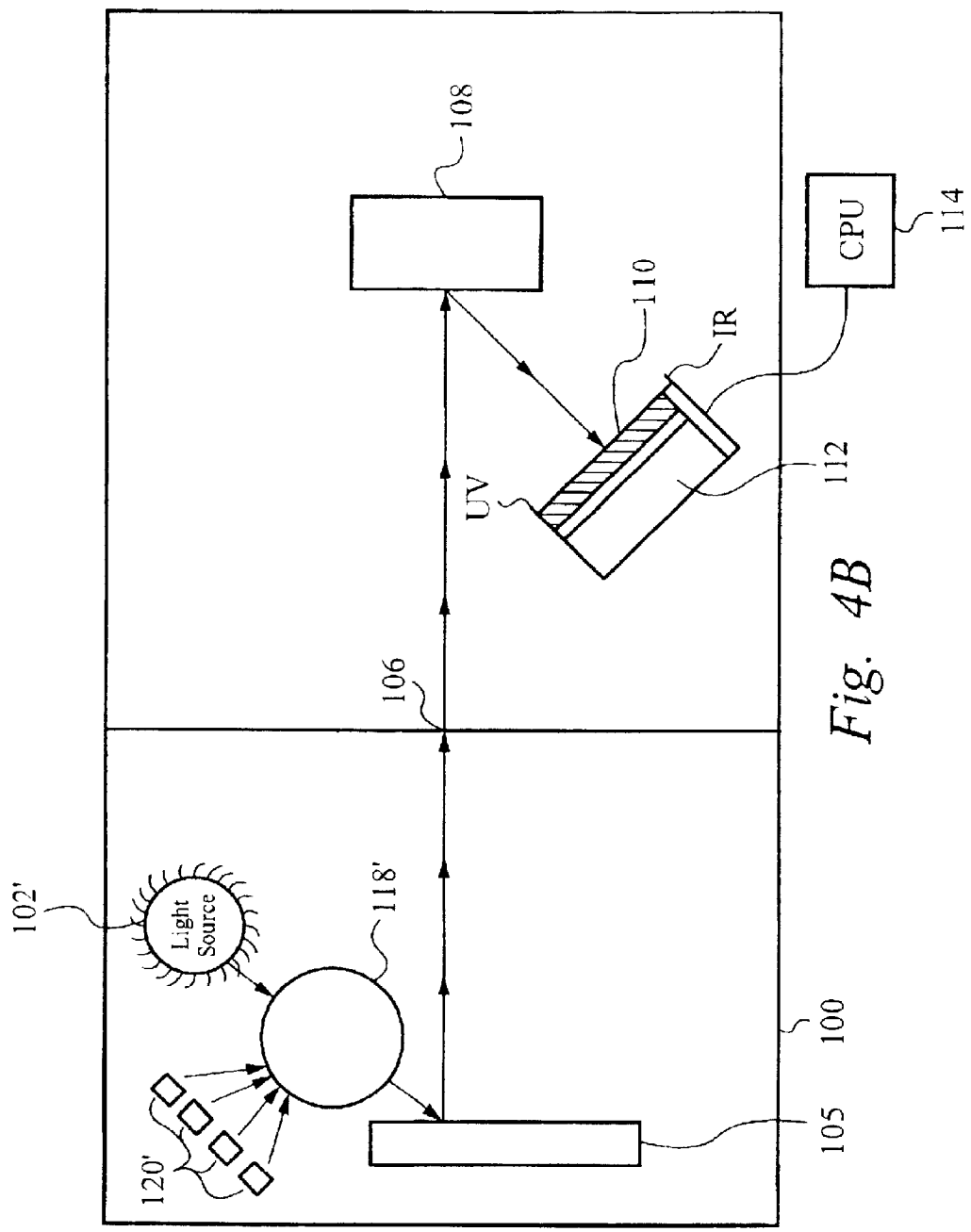
FIG. 4B illustrates a schematic of an alternative spectrophotometer for a reflective application in accordance with the present invention.

FIGS. 3A–3C illustrate different embodiments of a spectrophotometer for a transmission application in accordance with the present invention. Particularly, the transmission application primarily pertains to transmitting light through a transparent or translucent substrate material to determine a desired characteristic of the material medium. Preferably, the light source 102 passes light through the color balance filter 116, whereby the color balance filter 116 provides the desired wavelengths of light to the substrate 104, as shown in FIG. 3A.

Alternatively, the light source 102 as well as several light emitting diodes (LEDs) 120 beam light to an integrating sphere 118, whereby the integrating sphere 118 mixes the different sources of light and provides the mixed light to the substrate 104, as shown in FIG. 3B. In addition, as shown in the embodiment of FIG. 3B, a spatial filter 110 is coupled to the solid state diode array detector 112 to filter the light to include the desired spectral intensity distribution of wavelengths in the desired wavelength range.

The spatial filter 110 generally receives light from the light source 102 and inverts the amount of light intensity and silicon detector sensitivity of the light provided by the light source 102 as a function of wavelength. Specifically, since the light received by the spatial filter 110 has a stronger visible wavelength band than the ultraviolet and infrared bands, the spatial filter 110 attenuates the visible spectrum of light reaching the solid state diode array detector 112 until the ultraviolet and infrared wavelengths are clearly defined and readable by the detector 112. Thus, the solid state diode array detector 112 is programmed to wait for a predetermined amount of time to allow sufficient electrical charge accumulation before taking a reading of the received spectrum. This ensures that the ultraviolet and infrared wavelengths are sufficiently readable while oversaturation of the visible wavelengths in the solid state diode array detector 112 is avoided.

Alternatively, the light source 102 as well as several LEDS 120 beam light to a dichroic mirror 119, whereby the dichroic mirror mixes the different sources of light and provides the mixed light to the color balance filter 116, whereby the color balance filter 116 provides the desired wavelengths of light to the substrate 104, as shown in FIG. 3C.

As shown in FIGS. 3A–3C, from the light source, the light is then transmitted through the substrate 104 and passes through the slit aperture 106, whereby the slit aperture 106 converts the transmitted or modified light passed through the substrate 104 into a single beam. The beam of modified light travels from the slit aperture 106 to the diffraction grating 108, wherein the light spectrum is diffracted off the diffraction grating 108 at a predetermined angle. Preferably, the color balance filter 116 is used and the diffracted light spectrum travels to the solid state diode array detector 112. The solid state diode array detector 112 then provides data pertaining to the modified spectrum to the CPU 114. Alternatively, as shown in FIG. 3B, no color balance filter 116 is used and the diffracted light beam travels from the diffraction grating 108 to the spatial filter 110, whereby the spatial filter provides the modified light within the desired wavelength range to the solid state diode array detector 112.

Figure 4C:
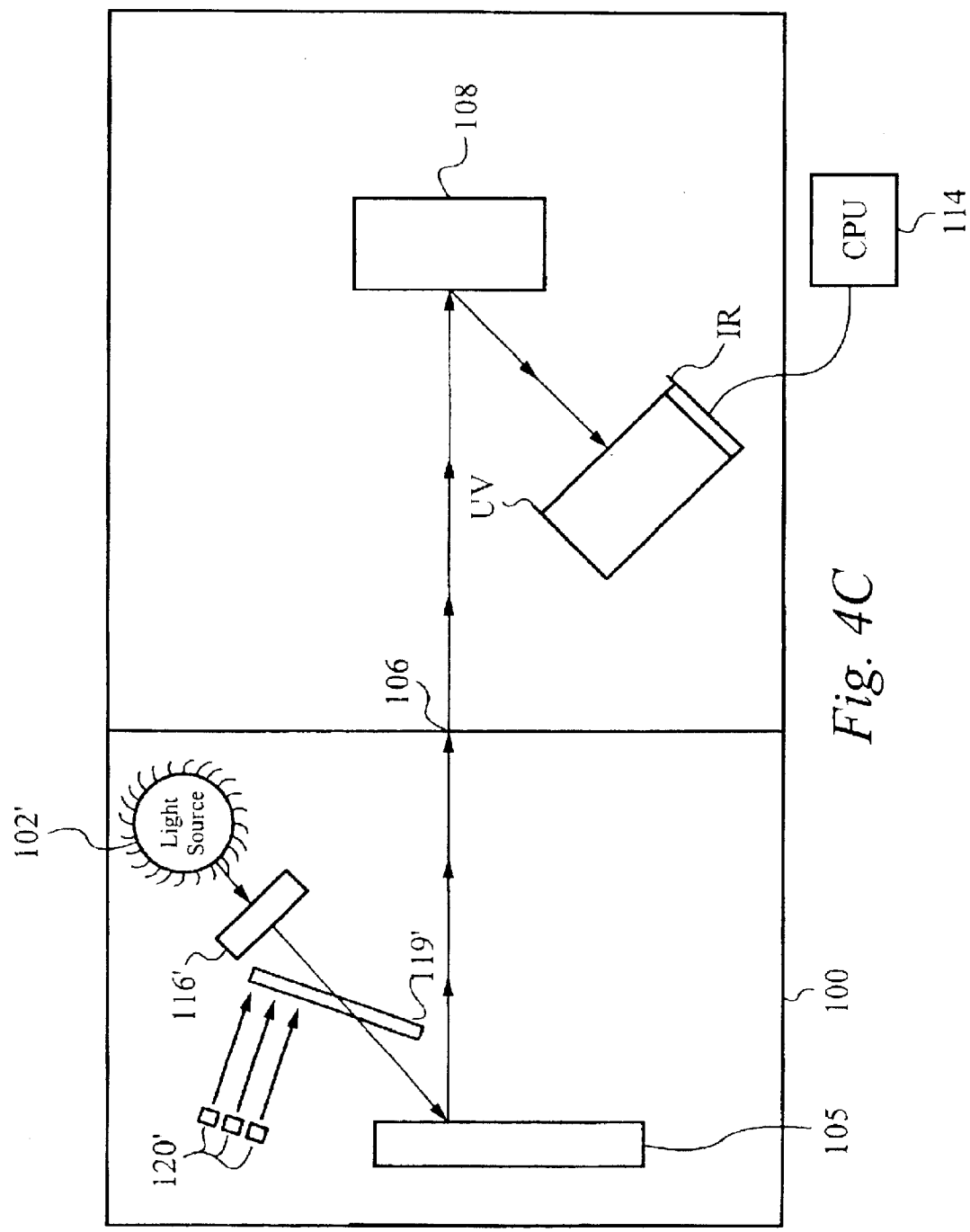
FIG. 4C illustrates a schematic of an alternative spectrophotometer for a reflective application in accordance with the present invention.

FIGS. 4A–4D illustrate different embodiments of a spectrophotometer for a reflective application in accordance with the present invention. Particularly, the reflective application primarily pertains to reflecting light off a material 105, such as an opaque surface, to determine a desired characteristic of the material 105. As shown in FIG. 4A, the light source 102' beams light through the color balance filter 116', whereby the color balance filter 116' provides the desired wavelengths of light to the material 105. Alternatively, the light source 102' as well as several light emitting diodes (LEDs) 120' beam light through an integrating sphere 118', whereby the integrating sphere 118' mixes the light from the different sources and provides the mixed light to the material 105, as shown in FIG. 4B. In addition, as shown in FIG. 4B, a spatial filter 110 is coupled to the solid state diode array detector 112 to filter the light to include only the wavelengths in the desired wavelength range. As discussed above, in any of these configurations, either the spatial filter 110 or the color balance filter 116 can be used. The color balance filter 116 is used in the preferred embodiment. Alternatively, the light source 102' as well as several LEDs 120' beam light to a dichroic mirror 119', whereby the dichroic mirror 119' mixes the light from the different sources and provides the mixed light to the material 105, as shown in FIG. 4C.

In each of the embodiments shown in FIGS. 4A–4D, the light is reflected off the material 105, whereby the reflected, modified light passes through the slit aperture 106. The slit aperture 106 converts the modified light into a single beam. The beam of modified light travels from the slit aperture 106 to the diffraction grating 108, wherein the light beam is diffracted off the diffraction grating 108 at a predetermined angle. Preferably, the color balance filter 116 is used and the diffracted light spectrum travels to the solid state diode array detector 112. The solid state detector then provides data pertaining to the modified spectrum to the CPU 114. Alternatively, the color balance filter 116 is not present and the diffracted light beam travels to the spatial filter 110, whereby the spatial filter provides a spectrum representative of the modified light to the solid state diode array detector 112.

Figure 4D:
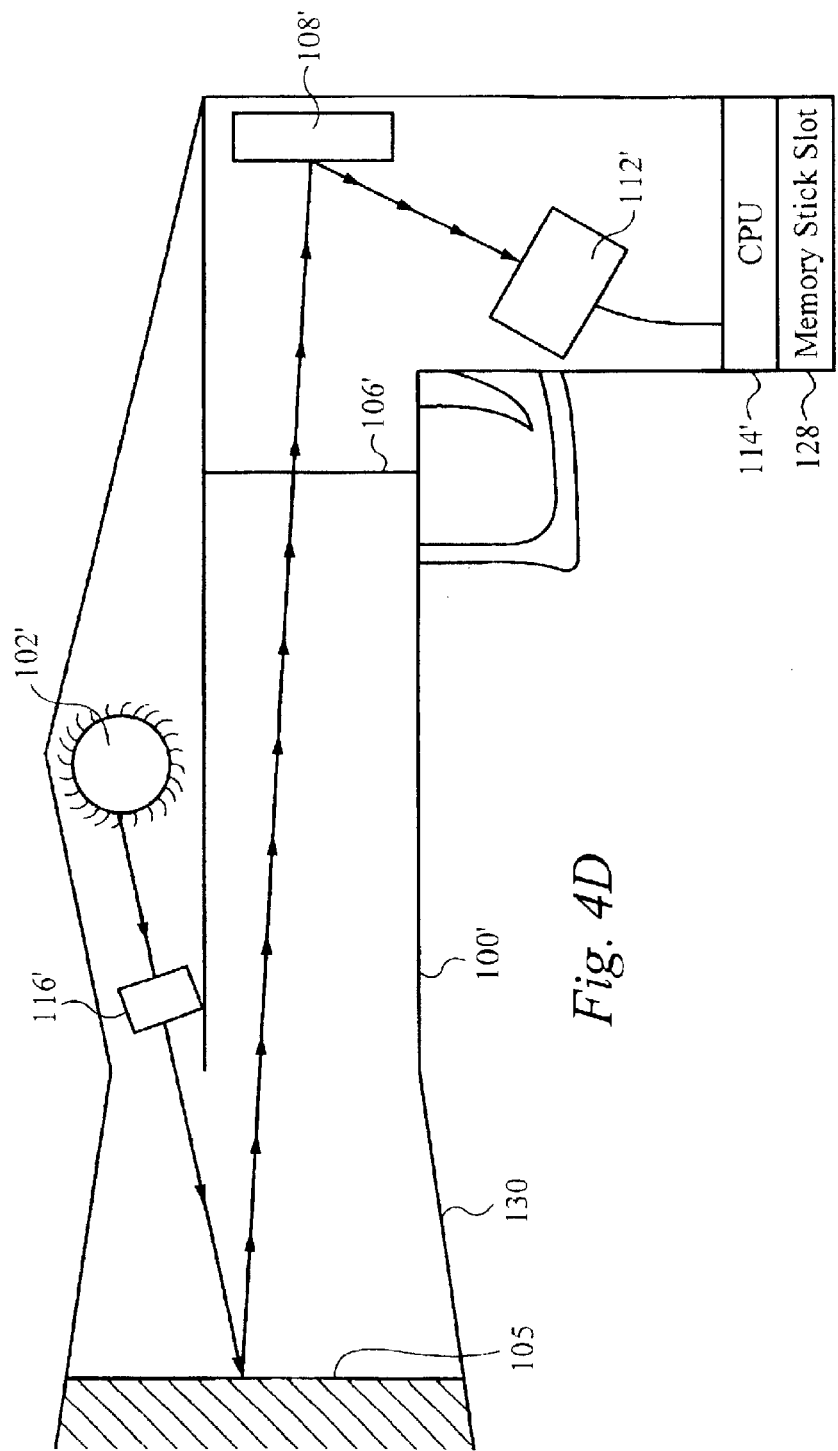
FIG. 4D illustrates a schematic of a preferred spectrophotometer for a reflective application in accordance with the present invention.

Preferably, the material is outside the spectrophotometer 100, whereby the user measures the material 105 by pointing the spectrophotometer 100 at the material 105, such as a wall. FIG. 4D illustrates the preferred embodiment of the spectrophotometer gun 100' for measuring the characteristics of an opaque material 105. As shown in FIG. 4D, the spectrophotometer 100' gun has a light tube 130 which prevents any light, besides the light emitted by the light source 102', from reflecting off the material 105. Thus, when measuring the material 105, such as wall color, the light tube 130 is abutted up against the wall, whereby only the light source 102' emits light that is reflected off the material 105. In addition, when calibrating the spectrophotometer gun 100', a neutral color screen, such as a white screen, is abutted up against the light tube 130, such that only the light source is reflected off the white screen and a reference spectrum is generated and stored in the CPU 114'.

As discussed above, the light from the light source 102' preferably passes through the color balance filter 116' which filters the light to only include the wavelengths in the desired wavelength range. As shown in FIG. 4D, the filtered light is reflected off the material 105 and the reflected light passes through the slit aperture 106' to the diffraction grating 108'. As shown in FIG. 4D, the diffraction grating 108' diffracts the modified light to the solid state diode detector array 112'. Alternatively, as shown in FIG. 4B, no color balance filter 116 is used and a spatial filter 100 (FIG. 4B) is coupled to the solid state diode array detector 112', whereby the spatial filter 110 (FIG. 4B) filters the light to include only the wavelengths within the desired wavelength range.

The spectrophotometer 100' preferably includes a CPU 114' which performs the necessary calculations to determine the desired integrated index. The spectrophotometer 100' also preferably includes a memory stick module 128' which allows the user to store any needed information, including the integrated indices, onto a memory stick (not shown). For example, the information on the memory stick (not shown) can be taken to a color matching station (not shown) to find a corresponding color match of the material being measured. It should be noted that the invention is not limited to only color matching and may be used for any other purpose.

Alternatively, the material 105 that is measured is placed within the spectrophotometer 100, as shown in FIG. 4A. An example of this is pointing the light source 102' within the spectrophotometer 100 up to a wall to determine the mean color index (see below) of the wall's paint color. The methods of calibrating and the measuring of the material for the reflective application is the same as in the transmission applications discussed below. However, for the reflective application, in relation to the methods described below, the light is reflected off of instead of transmitted through the material.

Figure 5:
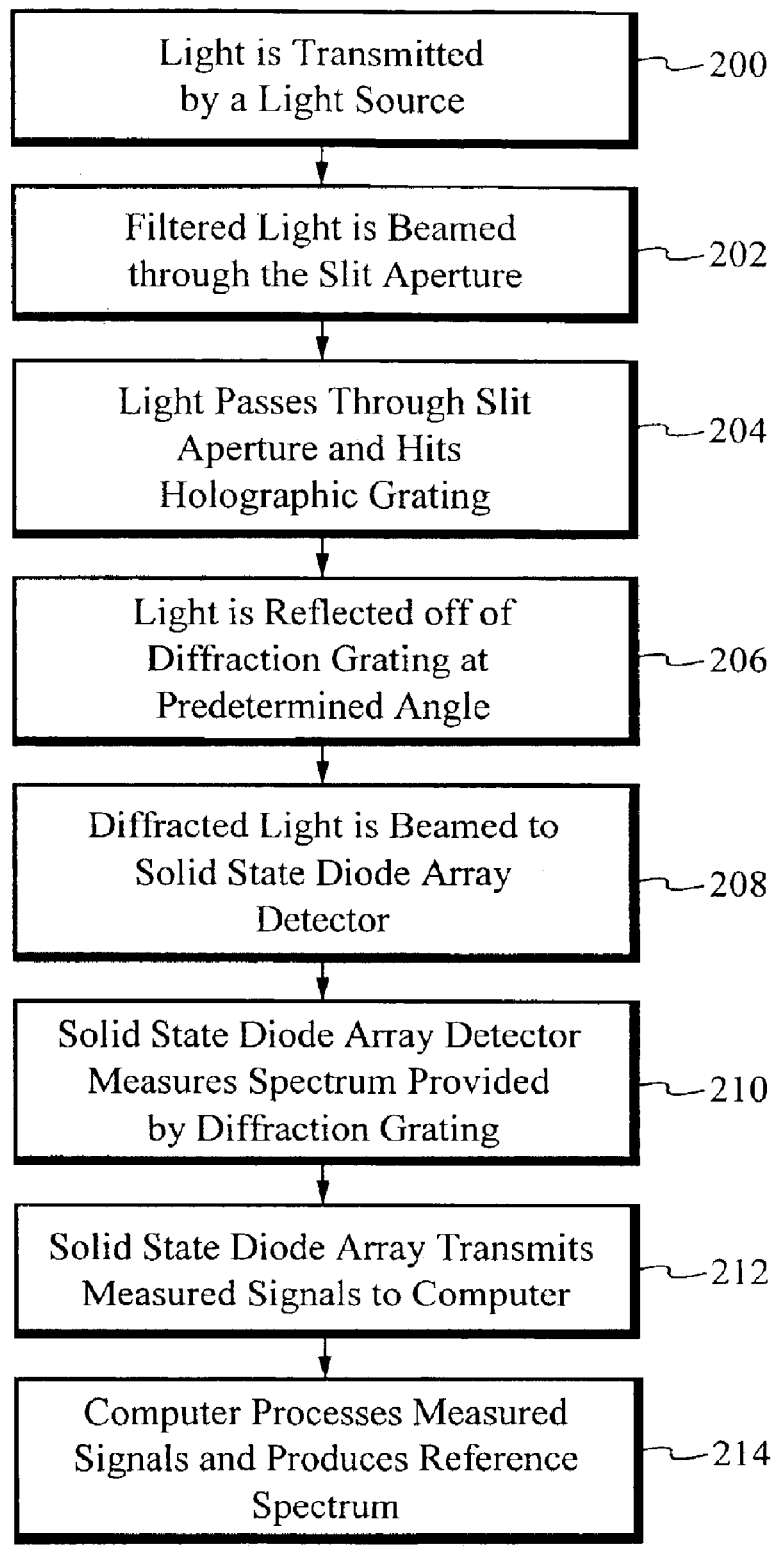
FIG. 5 illustrates a flow chart of the calibration process in accordance with the present invention.

The spectrophotometer 100 of the present invention is preferably first calibrated by the process shown in FIG. 5. A light source (FIG. 3A) or sources (FIGS. 3B, 3C) 102 emit light in the step 200. Alternatively, the light source 102 has any other desired voltage and can be configured a variety of ways as described above. The light from the light source 102 is preferably transmitted through a color balance filter 116. The filtered light is then passed to the slit aperture 106 in the step 202. Alternatively, the light from multiple light sources 102, 112 are mixed by a light mixing device (FIGS. 3A–4C), whereby the mixed light is passed to the slit aperture 106. The filtered light beam that is transmitted through the slit aperture 106 hits the diffraction grating 108 in the step 204. The light beam is then diffracted at a predetermined angle towards the solid state diode array detector 112 in the step 206.

As discussed above, preferably the spectrophotometer 100 includes a color balance filter 116, whereby a spatial filter (110) is alternatively used and positioned in front of the solid state diode array detector 112. Preferably, the light spectrum diffracted from the diffraction grating 108 is provided to the solid state diode array detector 112 in the step 208. Alternatively, light diffracted from the diffraction grating 108 is beamed to the spatial filter 110, whereby the spatial filter 110 provides a spectrum representative of the light beam to the solid state diode array detector 112. When calibrating the spectrophotometer 100, the diffraction grating 108 provides the light beam into a natural spectrum wherein ultra violet (UV) frequencies and infra-red (IR) frequencies are the boundaries of the spectrum, as shown in FIGS. 3A–3C. The solid state diode array detector 112 detects the spectrum and preferably uses Digital Signal Processor (DSP) technology to intelligently acquire measurement data associated with the reference spectrum in the step 210. Once the solid state diode array detector 112 acquires the reference measurement data, the reference data is sent to the CPU 114, as shown in the step 212. In calibration mode, the CPU 114 calculates a spectrum reference from the measured reference data in the step 214. The spectrum reference is then compared to an optical property of the substrate lens 104 or material 105 when the substrate lens 104 or material 105 is measured.

When the optical properties of a substrate lens 104 are measured to determine its integrated index, the substrate 104 is placed between the light source 102 and the slit aperture 106. Alternatively, when the optical properties of an opaque material 105 are measured to determine its integrated index, the material 105, is placed such that the light from the light source 102 reflects off the material 105 toward the slit aperture 106.

Figure 6:
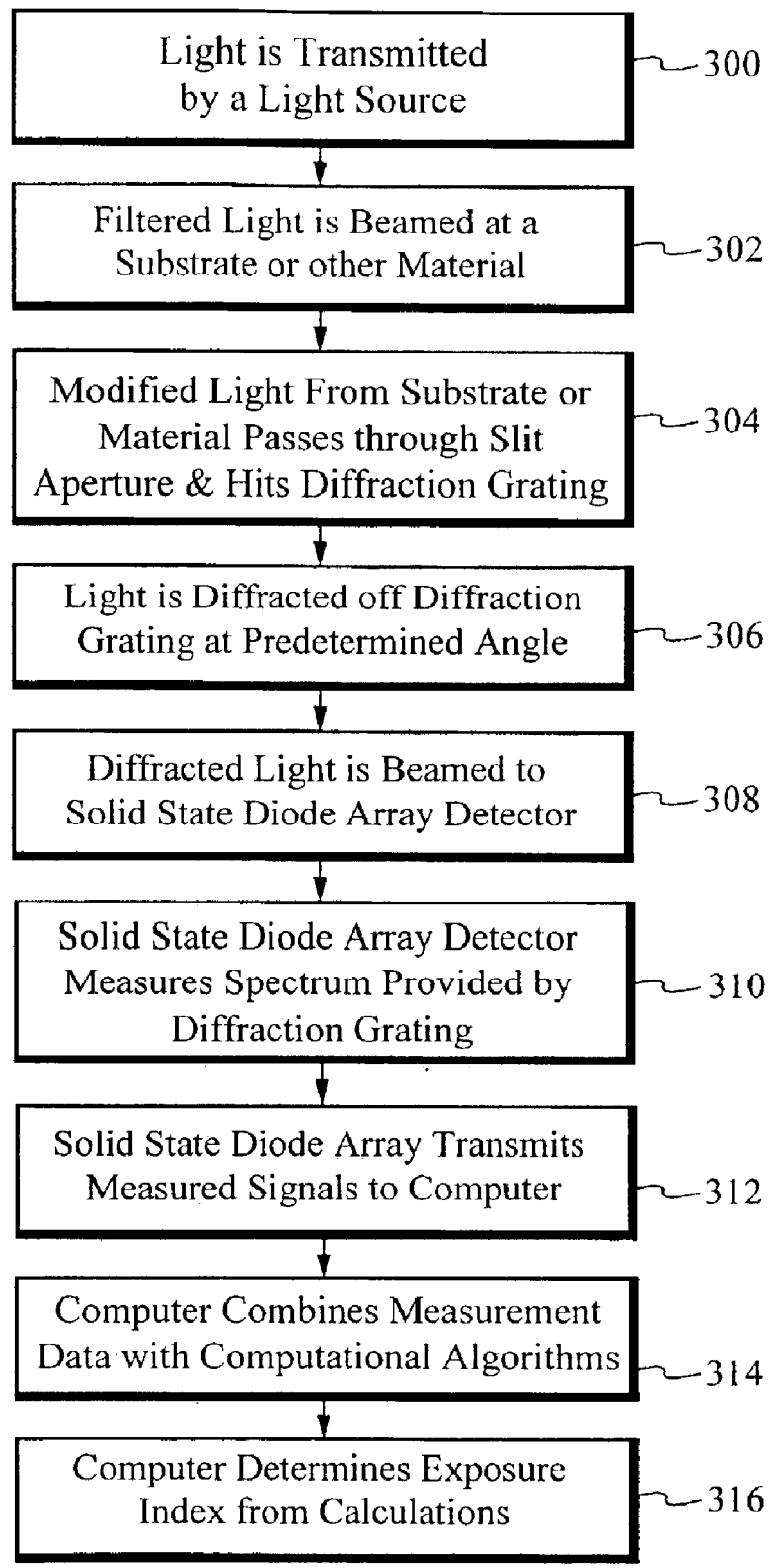
FIG. 6 illustrates a flow chart of the process of computing the integrated index process in accordance with the present invention.

FIG. 6 illustrates a flow chart describing the process of determining an integrated index for the substrate lens 104 or other product material 105. The light is transmitted from the light source 102 in the step 300 and is preferably filtered by the color balance filter 116. Alternatively, no color balance filter 116 is used and a spatial filter 110 is used instead. The light passes through the substrate lens 104 or is reflected off the material 105 in the step 302. The substrate 104 or material 105 will typically remove one or more wavelength bands that are emitted from the light source 102, whereby the modified light passes through the slit aperture 106. The beam of modified light which passes through the slit aperture 106 preferably hits the diffraction grating 108 in the step 304. The modified light is then diffracted at a predetermined angle towards the solid state diode array detector 112 in the step 306. As shown in FIG. 3B, the spatial filter 110 is alternatively positioned in front of the solid state diode array detector 112, such that the modified light reflected from the diffraction grating 108 is received at the spatial filter 110.

Once the solid state diode array detector 112 detects the modified spectrum from the diffraction grating 108 and measures the modified spectrum in the step 310. The measurement data of the substrate 104 or material 105 specifically relates to the change in intensity of the modified light in comparison to the calibrated light. In addition, the measurement data of the substrate 104 specifically relates to wavelengths which are transmitted, reflected or blocked by the substrate in comparison to the wavelengths present in the calibrated light. Once the solid state diode array detector 112 acquires this measurement data, such as a transmission value (T), the data is sent to the CPU 114, preferably as digital signals in the step 312, whereby the CPU 114 preferably stores the data.

The CPU 114 combines the received spectrophotometric measurements data of the product with a predetermined set of equations in the step 314. This combination is used to compute the integrated index in the step 316. This index is displayed to the user in either a numerical form or in a graphical form. Alternatively, the index is sent via the world wide web to a designated recipient.

The calculation performed by the CPU depends on what type of integrated index is desired for the product being measured. For example, in order to determine the integrated index relating to optical transmission properties of a transparent product, a predetermined set of calculations are used to calculate an "integrated ocular exposure index" as shown below. Also, to determine the integrated index relating to optical transmission properties of optical substrates, another predetermined set of equations are used to calculate an "integrated photopic response index" and/or an "integrated scotopic response index" for wavelength specific ocular photopic and scotopic response functions, as shown below. Other calculations associated with transmission properties of other types of media are mentioned below.

For certain integrated indices, reference ambient solar or illumination source irradiance values provided by the light source 102, 120 are weighed against product transmission/reflection spectra of the product to calculate whether an appropriate level of exposure protection is being provided by the product. As shown below, the measurements taken of the product's material are used to calculate and determine several different types of integrated indices.

To determine the integrated index relating to optical transmission properties of a measured product, the equation below is used to calculate an "Ocular Protection Index" or OPI. The OPI is preferably taken for products characterized as including a transparent material. Alternatively, the OPI is taken for products characterized as including a translucent material. The specific equation (1) for calculating the OPI is shown below.

$$OPI = 100 \left[ 1 - \left( \frac{\sum_{\lambda_1}^{\lambda_2} P_\lambda T_\lambda (S_\lambda + B_\lambda + R_\lambda)}{\sum_{\lambda_1}^{\lambda_2} P_\lambda (S_\lambda + B_\lambda + R_\lambda)} \right) \right] \quad (1)$$

As shown in equation (1), the numerator is calculated for the variables at each wavelength λ within the wavelength range, whereby the wavelength range is between the minimum wavelength $\lambda_1$ and the maximum wavelength $\lambda_2$. Similarly, the denominator is calculated for the variables at each wavelength λ within the same wavelength range. As shown in equation (1), the sum of the numerator values over the range are divided by the sum of the denominator values over the range. Preferably, as shown in equation (1), the divided value is subtracted from a whole value of 1 to give a result which signifies the amount of exposure that the measured lens protects against ("protection value"). Alternatively, the divided value result is not subtracted from the whole value 1, whereby the divided value result represents the amount of exposure allowed by the measured lens ("exposure value"). In addition, as shown in equation (1), the protection value is multiplied by a value of 100 to provide a rounded number. Alternatively, the protection value or exposure value is not multiplied by the value of 100.

The boundaries of the wavelength range to calculate the OPI are a minimum wavelength $\lambda_1$ in the range of 300–320 nm and the maximum wavelength $\lambda_2$ in the range of 900–1400 nm. Preferably, the values of each variable in each of the equations discussed herein is taken in wavelength increments of 5 nm. Alternatively, the value of each variable in each of the equations discussed herein is taken in any other wavelength increments. The value $P_\lambda$ is the ambient spectral irradiance of the light source 102 as a function of wavelength λ. For example, a value for $P_\lambda$ at wavelength 315 nm is 0.0764 W/(cm$^2$-$\mu$m). However, this value is for example purposes only, and specific values of the $P_\lambda$ factor are available in appropriate reference materials such as NASA Technical Report R351. In addition, $T_\lambda$ is the measured lens transmission value of the product as a function of wavelength λ. $B_\lambda$ is the blue-light hazard factor dependent on wavelength λ and the value $R_\lambda$ is the retinal thermal hazard factor also dependent on a function of wavelength λ. Further, $S_\lambda$ is the UV spectral effectiveness factor dependent on wavelength λ. For example, for a wavelength of 315 nm, the value for $B_\lambda$ is 0.01. However, this value is for example purposes, and specific values of the $B_\lambda$ and $R_\lambda$ factors are available in appropriate reference materials.

Another integrated index that can be calculated from the measurements of the measured product is the "Ultraviolet Protection Index" or UPI. The UPI provides a quantified value representative of the amount of UV rays that the product material allows through or protects against. The UPI value is preferably taken for products characterized as having a transparent material, including, but limited to, sunglass lenses, eyeglass lenses, windows, window materials, optical substrates, and optical coatings on substrates, optical instrument components, optical filters, industrial safety screens, welding safety filters and welding safety screens. In addition, other industrial applications are contemplated to prevent occupational exposure to intense artificial sources of UV such as instrument lamps and arc welding apparatus. Alternatively, the UPI is taken for products characterized as having a translucent or opaque material. The specific equation (2) for calculating the UPI value is shown below.

$$UPI = 100 \left[ 1 - \left( \frac{\sum_{\lambda_1}^{\lambda_2} P_\lambda T_\lambda S_\lambda}{\sum_{\lambda_1}^{\lambda_2} P_\lambda S_\lambda} \right) \right] \quad (2)$$

As shown in equation (2), the numerator is calculated for the variables at each wavelength λ within the wavelength range, whereby the wavelength range is between the minimum wavelength $\lambda_1$ and the maximum wavelength $\lambda_2$.

Similarly, the denominator is calculated for the variables at each wavelength λ within the same wavelength range. As shown in equation (2), the sum of the numerator values over the range are divided by the sum of the denominator values over the range. Preferably, as shown in equation (2), the divided value is subtracted from a whole value of 1 to give a result which signifies the amount of exposure that the measured lens protects against ("protection value"). Alternatively, the divided value result is not subtracted from the whole value 1, whereby the divided value result represents the amount of exposure allowed by the measured lens ("exposure value"). In addition, as shown in equation (2), the protection value is multiplied by a value of 100 to provide a rounded number. Alternatively, the protection value or exposure value is not multiplied by the value of 100.

The boundaries of the wavelength range for the UPI are such that a minimum wavelength $\lambda_1$ is in the range of 180–320 nm and the maximum wavelength $\lambda_2$ is approximately 500 nm. Again, the value $P_\lambda$ is the ambient spectral irradiance of the light source 102 as a function of wavelength λ. In addition, the value $T_\lambda$ is the measured lens transmission value of the product as a function of wavelength λ. $B_\lambda$ is the blue-light hazard factor dependent on wavelength λ. whereby specific values of the $B_\lambda$ factor are available in appropriate reference materials such as the ACGIH 2001 Handbook of TLVs® and BEIs®.

Another integrated index that can be calculated from the measurements taken of the product is the "integrated infrared (IR) exposure index" or IPI. The IPI provides a quantified value representative of the amount of IR rays that the product material allows through or protects against. The IPI value is preferably taken for products characterized as having a transparent material, including, but not limited to, windows, window materials, optical substrates, and optical coatings on substrates. Alternatively, the IPI is taken for products characterized as a translucent or opaque material. The specific equation (3) for calculating the IPI value is shown below.

$$IPI = 100\left[1 - \left(\frac{\sum_{\lambda_1}^{\lambda_2} P_\lambda T_\lambda R_\lambda}{\sum_{\lambda_1}^{\lambda_2} P_\lambda R_\lambda}\right)\right] \quad (3)$$

As shown in equation (2), the numerator is calculated for the variables at each wavelength λ within the wavelength range, whereby the wavelength range is between the minimum wavelength $\lambda_1$ and the maximum wavelength $\lambda_2$. Similarly, the denominator is calculated for the variables at each wavelength λ within the same wavelength range. As shown in equation (2), the sum of the numerator values over the range are divided by the sum of the denominator values over the range. Preferably, as shown in equation (2), the divided value is subtracted from a whole value of 1 to give a result which signifies the amount of exposure that the measured lens protects against ("protection value"). Alternatively, the divided value result is not subtracted from the whole value 1, whereby the divided value result represents the amount of exposure allowed by the measured lens ("exposure value"). In addition, as shown in equation (2), the protection value is multiplied by a value of 100 to provide a rounded number. Alternatively, the protection value or exposure value is not multiplied by the value of 100.

The boundaries of the wavelength range are such that a minimum wavelength $\lambda_1$ is in the range of 300–385 nm and the maximum wavelength $\lambda_2$ is in the range of 900–1400 nm. Again, the variables $P_\lambda$ and $T_\lambda$ are the same as in the above equations. The value $R_\lambda$ is the retinal thermal hazard factor that is dependent on the wavelength λ determined from the light emitted by the light source 102. For example, for a wavelength of 1400 nm, the value of $R_\lambda$ is 0.2. However, this value is for example purposes, and the specific values of the $R_\lambda$ factor are available in appropriate reference materials such as the ACGIH 2001 Handbook of TLVs® and BEIs®.

Yet, another integrated index that can be calculated from the measurements taken of the product is the "integrated aphakic exposure index" or API. The API provides a quantified value representative of the amount of exposure of harmful rays that the product allows through or protects against for a person having a cataract condition. The aphakic function relates to radiation exposure issues for persons who have had a lens removed during cataract surgery and who are thus subject to unique ocular radiation exposure issues. The API value is preferably taken for products characterized as a transparent material. Alternatively, the API is taken for products characterized as an translucent or opaque material. The specific equation (4) for calculating the API value is shown below.

$$API = 100\left[1 - \left(\frac{\sum_{\lambda_1}^{\lambda_2} P_\lambda T_\lambda A_\lambda}{\sum_{\lambda_1}^{\lambda_2} P_\lambda A_\lambda}\right)\right] \quad (4)$$

As shown in equation (4), the numerator is calculated for the variables at each wavelength λ within the wavelength range, whereby the wavelength range is between the minimum wavelength $\lambda_1$ and the maximum wavelength $\lambda_2$. Similarly, the denominator is calculated for the variables at each wavelength λ within the same wavelength range. As shown in equation (4), the sum of the numerator values over the range are divided by the sum of the denominator values over the range. Preferably, as shown in equation (4), the divided value is subtracted from a whole value of 1 to give a result which signifies the amount of exposure that the measured lens protects against ("protection value"). Alternatively, the divided value result is not subtracted from the whole value 1, whereby the divided value result represents the amount of exposure allowed by the measured lens ("exposure value"). In addition, as shown in equation (4), the protection value is multiplied by a value of 100 to provide a rounded number. Alternatively, the protection value or exposure value is not multiplied by the value of 100.

The boundaries of the wavelength range are such that a minimum wavelength $\lambda_1$ is in the range of 300–305 nm and the maximum wavelength $\lambda_2$ is approximately 700 nm. The value $A_\lambda$ is the aphakic hazard factor determined as a function of wavelength λ from the light emitted by the light source 102. For example, for a wavelength of 305 nm, the value of $A_\lambda$ is 6. However, this value is for example purposes, and the specific values of the $A_\lambda$ factor are available in appropriate reference materials such as the ACGIH 2001 Handbook of TLVs® and BEIs®. Again, the variables $P_\lambda$ and $T_\lambda$ are the same as in the above equations.

Another integrated index that can be calculated from the measurements taken of the product is the "Erythemal Protection Index" or EPI. The EPI provides a quantitative measure of the integrated erythemal protection index as a percent of the incident radiation spectrum. Preferably, the incident radiation spectrum of interest is the ambient solar radiation spectrum provided by the light source 102. The EPI value is preferably taken for products characterized as having an opaque material. Specifically, the EPI value characterizes textile products including, but not limited to, sun-block lotions, cosmetics, clothing, swimsuits, umbrellas, and outdoor sunscreens. Alternatively, the EPI is taken for products characterized as a transparent or translucent material. The specific equation (5) for calculating the EPI value is shown below.

$$EPI = 100\left[1 - \left(\frac{\sum_{\lambda_1}^{\lambda_2} P_\lambda T_\lambda E_\lambda}{\sum_{\lambda_1}^{\lambda_2} P_\lambda E_\lambda}\right)\right] \quad (5)$$

As shown in equation (5), the numerator is calculated for the variables at each wavelength $\lambda$ within the wavelength range, whereby the wavelength range is between the minimum wavelength $\lambda_1$ and the maximum wavelength $\lambda_2$. Similarly, the denominator is calculated for the variables at each wavelength $\lambda$ within the same wavelength range. As shown in equation (5), the sum of the numerator values over the range are divided by the sum of the denominator values over the range. Preferably, as shown in equation (5), the divided value is subtracted from a whole value of 1 to give a result which signifies the amount of exposure that the measured lens protects against ("protection value"). Alternatively, the divided value result is not subtracted from the whole value 1, whereby the divided value result represents the amount of exposure allowed by the measured lens ("exposure value"). In addition, as shown in equation (5), the protection value is multiplied by a value of 100 to provide a rounded number. Alternatively, the protection value or exposure value is not multiplied by the value of 100.

The boundaries of the wavelength range are such that a minimum wavelength $\lambda_1$ is in the range of 185 nm–300 nm and the maximum wavelength $\lambda_2$ is in the range of 320–500 nm. The value $E_\lambda$ is the erythemal response factor determined as a function of wavelength $\lambda$ from the light emitted by the light source 102. Again, the variables $P_\lambda$ and $T_\lambda$ are the same as in the above equations.

Another integrated index that can be calculated from the measurements taken of the product is the "Heat Flux Index" or HFI. The HFI provides a measure of the total radiant heat flux which is transmitted by the glazing material or substrate material of the product as a percent of the incident heat flux of the light emitted by the light source 102. The HFI value is preferably taken for products characterized as transparent or translucent materials. Specifically, the HFI value is applied to windows, window materials, optical substrates, and optical coatings on substrates. Alternatively, the HFI is taken for products characterized as an opaque material. The specific equation (6) for calculating the HFI value is shown below.

$$HFI = 100\left[\frac{\left(\sum_{\lambda_1}^{\lambda_2} P_\lambda T_\lambda Q_\lambda\right)}{\left(\sum_{\lambda_1}^{\lambda_2} P_\lambda Q_\lambda\right)}\right] \quad (6)$$

As shown in equation (6), the numerator is calculated for the variables at each wavelength $\lambda$ within the wavelength range, whereby the wavelength range is between the minimum wavelength $\lambda_1$ and the maximum wavelength $\lambda_2$. Similarly, the denominator is calculated for the variables at each wavelength $\lambda$ within the same wavelength range. As shown in equation (6), the sum of the numerator values over the range are divided by the sum of the denominator values over the range. Preferably, the divided value result represents the amount of exposure allowed by the measured lens ("exposure value"). In addition, as shown in equation (6), the exposure value is multiplied by a value of 100 to provide a rounded number. Alternatively, the exposure value is not multiplied by the value of 100.

The boundaries of the wavelength range are such that a minimum wavelength $\lambda_1$ is approximately 300 nm and the maximum wavelength $\lambda_2$ is in the range of 1000–12000 nm. The value $Q_\lambda$ is the energy absorption factor determined as a function of wavelength $\lambda$ from the light emitted by the light source 102. The energy absorption factor represents the black-body absorption parameter characterizing the extent to which incident light is absorbed and converted to heat. For example, this parameter could be used to characterize the interior surfaces of rooms in buildings for which glazing infra-red shielding efficiency is analyzed. The specific values of the $Q_\lambda$ factor depend on the type of material or surface being analyzed. Again, the variables $P_\lambda$ and $T_\lambda$ are the same as in the above equations.

Regarding ocular exposure to ultraviolet (UV), visible, and infrared (IR) radiation, "spectral weighting functions" and "hazard functions" for discrete parts of the optical radiation spectrum have been developed. The spectral weighting functions are used to calculate a threshold exposure duration for a light source of known intensity, which is the integrated spectral radiance ($L_\lambda$) as a function of wavelength. The product of the (integrated) source radiance, the wavelength-specific spectral hazard functions, and the time of exposure is summed over the spectral range of the source in order to calculate the Threshold Limit Values or TLVs and permissible exposure times for the particular light source which has been previously characterized.

It should be noted that although equations (1)–(6) shown above preferably utilize the ambient spectral irradiance value $P_\lambda$ to characterize a material in relation to a natural illumination source, it is contemplated that the illumination source irradiance value $L_\lambda$ may alternatively be used in the above equations to characterize the material in relation to an artificial illumination source.

Another integrated index that can be calculated from the measurements taken of the product is the "photopic response index" or PRI. Photopic vision is daylight vision in which the human eye can see colors. The PRI provides a quantified measure of the certain colors which are more perceivable by the human eye through a particular lens. An example in which the PRI can be used is to rate a lens's ability to separate out desired colors which allows the user to distinguish between the colors in a traffic signal light. Another example in which the PRI can be used is to quantify the actual colors (red, yellow, green) in the traffic signal light, such that colors in the traffic signal lights are able to catch attention of the user who is or is not wearing lenses. It should be noted that the PRI is not limited to only traffic applications and can be used for any other application. The PRI value is preferably taken for transparent or translucent materials, such as optical lenses and filters. Alternatively, the PRI value is taken for opaque materials. The specific equation (7) for calculating the PRI value is shown below.

$$PRI = \left[ \frac{\left( \sum_{\lambda_1}^{\lambda_2} PH_\lambda T_\lambda L_\lambda \right)}{\left( \sum_{\lambda_1}^{\lambda_2} PH_\lambda L_\lambda \right)} \right] \quad (7)$$

As shown in equation (7), the numerator is calculated for the variables at each wavelength λ within the wavelength range, whereby the wavelength range is between the minimum wavelength $\lambda_1$ and the maximum wavelength $\lambda_2$. Similarly, the denominator is calculated for the variables at each wavelength λ within the same wavelength range. As shown in equation (7), the sum of the numerator values over the range are divided by the sum of the denominator values over the range. The boundaries of the wavelength range are such that a minimum wavelength $\lambda_1$ is approximately 400 nm and the maximum wavelength $\lambda_2$ is in the range of 700–750 nm. The value $PH_\lambda$ is the ocular photopic response factor which is determined from specific values available in appropriate reference materials such as the CIE 1931 Standard Observer. The value $L_\lambda$ is the illumination source irradiance value is dependent on the wavelength λ and is determined from the light emitted by the light source 102. The $L_\lambda$ value varies significantly with different sources and refers to the "color temperature" of various lamps. The $L_\lambda$ factor, relating to illumination source radiation, is used for an artificial light source whereas the $P_\lambda$ factor, relating to ambient solar irradiance, is used for natural sunlight. Specific values of the $L_\lambda$ factor for each corresponding wavelength can be found in appropriate reference materials for a desired artificial lamp. The variable $T_\lambda$ is the lens transmission value of the product's material.

In addition, another integrated index that can be calculated from the measurements taken of the product is the "scotopic response index" or SRI. The scotopic vision is the ability of the human eye to see objects in darkness and dimness, whereby the vision is mainly monochromatic. The SRI provides a quantified measure of the certain shades of gray or colors in the dark which are more perceivable by the human eye through a particular lens. An example in which the SRI can be used is to rate a lens's ability to separate out desired colors in a road sign which allows the user to see the sign in darkness when wearing eyeglass lenses. Another example in which the SRI can be used is to quantify the actual colors in the sign, such that colors in the sign are able to catch attention of the user who is or is not wearing lenses. It should be noted that the SRI is not limited to only traffic applications and can be used for any other application. The SRI value is preferably taken for transparent and translucent materials, such as optical products. Alternatively, the SRI value is taken for opaque materials, such as the road sign. The specific equation (8) for calculating the SRI value is shown below.

$$SRI = \left[ \frac{\left( \sum_{\lambda_1}^{\lambda_2} SC_\lambda T_\lambda L_\lambda \right)}{\left( \sum_{\lambda_1}^{\lambda_2} SC_\lambda L_\lambda \right)} \right] \quad (8)$$

As shown in equation (8), the numerator is calculated for the variables at each wavelength λ within the wavelength range, whereby the wavelength range is between the minimum wavelength $\lambda_1$ and the maximum wavelength $\lambda_2$. Similarly, the denominator is calculated for the variables at each wavelength λ within the same wavelength range. As shown in equation (8), the sum of the numerator values over the range are divided by the sum of the denominator values over the range. The boundaries of the wavelength range are such that a minimum wavelength $\lambda_1$ is approximately 400 nm and the maximum wavelength $\lambda_2$ is in the range of 700–750 nm. The value $SC_\lambda$ is the ocular scotopic response factor which is determined from specific values found in appropriate reference materials such as the CIE 1931 Standard Observer. Again, the value $L_\lambda$ is the illumination source irradiance value dependent on the wavelength λ and is determined from the light emitted by the light source 102. The variable $T_\lambda$ is the measured transmission value of the product's material.

A "visual response index" or VRI value is used to quantify the overall polychromatic and monochromatic characteristics of a product material and is calculated using both $SC_\lambda$ and $PH_\lambda$ factors that are discussed above. The VRI value quantifies a value which accurately characterizes color discriminations in general of specific substrates, coatings, light sources, signals, filters, and other product transparent and translucent materials. Alternatively, the VRI characterizes color discriminations in opaque materials. The same variables used in equation (8) also applies here. The boundaries of the wavelength range for the equation shown below are such that a minimum wavelength $\lambda_1$ is approximately 400 nm and the maximum wavelength $\lambda_2$ is in the range of 700–750 nm. The specific equation (9) for calculating the VRI shown below.

$$VRI = \left[ \frac{\left( \sum_{\lambda_1}^{\lambda_2} (PH_\lambda + SC_\lambda) T_\lambda L_\lambda \right)}{\left( \sum_{\lambda_1}^{\lambda_2} (PH_\lambda + SC_\lambda) L_\lambda \right)} \right] \quad (9)$$

Another integrated index that can be calculated from the measurements taken of the product is the "Differential Color Index" or DCI. The DCI value provides a quantified value which represents the amount of comparison between colors of different materials. Preferably, such product materials include, but are not limited to paints, coatings, filters, optical media, optical coatings and other materials.

Generally, the DCI value is determined by calculating the numerator value by taking the difference between the transmitted or reflected values of a reference material and the transmitted or reflected values of a measured material for each wavelength. The difference is then multiplied with the variables shown in equations below and summed over the desired wavelength range. The denominator value is calculated by multiplying the variables for each wavelength in the same wavelength range. The summed numerator and the denominator values are then divided to generate a DCI value. As shown below, equations (10)–(12) are used to calculate the DCI of the three primary colors based on the wavelength range:

$$DCI_{yellow} = \left[ \frac{\sum_{520}^{620} L_\lambda PH_\lambda (T_{r_\lambda} - T_{m_\lambda})}{\sum_{520}^{620} L_\lambda PH_\lambda T_{r_\lambda}} \right] \quad (10)$$

$$DCI_{red} = \left[ \frac{\sum_{620}^{770} L_\lambda PH_\lambda (T_{r_\lambda} - T_{m_\lambda})}{\sum_{620}^{770} L_\lambda PH_\lambda T_{r_\lambda}} \right] \quad (11)$$

$$DCI_{blue} = \left[ \frac{\sum_{400}^{520} L_\lambda PH_\lambda (T_{r_\lambda} - T_{m_\lambda})}{\sum_{400}^{520} L_\lambda PH_\lambda T_{r_\lambda}} \right] \quad (12)$$

As shown in the above equations,(10)–(12), the value $PH_{80}$ is the ocular photopic response factor dependent on wavelength $\lambda$ determined from the light emitted. The variable $L_\lambda$ is the illumination source irradiance factor dependent on wavelength $\lambda$ determined from the light emitted. In addition, the value $Tr_\lambda$ is the transmitted or reflected spectrum of the reference product material or unfiltered light as a function of wavelength $\lambda$. Furthermore, the value $Tm_\lambda$ is the transmitted or reflected spectrum of the measured product material as a function of the wavelength $\lambda$. As shown above, the boundaries of the wavelength range for the blue band in equation (10) are such that a minimum wavelength $\lambda_1$ is approximately 400 nm and the maximum wavelength $\lambda_2$ is 520 nm. In addition, the boundaries of the wavelength range for the yellow band in equation (11) are such that a minimum wavelength $\lambda_1$ is approximately 520 nm and the maximum wavelength $\lambda_2$ is 620 nm. Further, the boundaries of the wavelength range of the red band in equation (12) are such that a minimum wavelength $\lambda_1$ is approximately 620 nm and the maximum wavelength $\lambda_2$ is 770 nm.

In addition, the present invention can combine the spectrophotometric measurements of transmitted or reflected light with the equation shown below in equation (13) to accurately determine a "center wavelength" or dominant wavelength which determines the perceived color of the measured product material. The equation below determines the center wavelength as a "Mean Color Index" or MCI. The product material preferably includes, but not limited to, opaque material such as paints, coatings, filters, optical media, and optical coatings. Alternatively, the material is a transparent or translucent material. In the case of complex multimode color spectra corresponding to basic applications, such as paint matching or paint mixing colors, multiple indices are used to correlate each of the basic component spectra to the final mixed color. The MCI value is calculated as shown in equation (13).

$$MCI = \left[ \frac{\left( \sum_{\lambda_1}^{\lambda_2} L_\lambda T_{m_\lambda} \right)}{\left( \sum_{\lambda_1}^{\lambda_2} L_\lambda \right)} \right] = \lambda_{center} \quad (13)$$

As shown in equation (13), the numerator is calculated for the variables at each wavelength $\lambda$ within the wavelength range, whereby the wavelength range is between the minimum wavelength $\lambda_1$ and the maximum wavelength $\lambda_2$. Similarly, the denominator is calculated for the variables at each wavelength $\lambda$ within the same wavelength range. As shown in equation (13), the sum of the numerator values over the range are divided by the sum of the denominator values over the range. The boundaries of the wavelength range are such that a minimum wavelength $\lambda_1$ is approximately 400 nm and the maximum wavelength $\lambda_2$ is in the range of 700–750 nm. As shown in equation (13), the $L_1$ value is an illumination source irradiance value dependent on the wavelength $\lambda$ determined from the light being emitted by the light source 102. The $Tm_\lambda$ variable is the transmitted or reflected spectrum of the measured product material.

An example of how an integrated index, such as the OPI, is calculated will now be discussed. Initially, the spectrophotometer 100 of the present invention is calibrated whereby the light source 102 is conditioned to emit light between the wavelength range of 320 nm ($\lambda_1$) and 900 nm ($\lambda_2$). As discussed above, in any of these configurations, either the spatial filter 110 or the color balance filter 116 can be used to condition the light within the desired wavelength range. The color balance filter 116 is used in the preferred embodiment. Preferably, the color balance filter 116 filters out the desired wavelength range of 320 nm–900 nm, whereby the conditioned light is passed to the diffraction grating 108. The diffraction grating 108 diffracts the light as a spectrum at a predetermined angle towards the solid state diode array detector 112.

The solid state diode array detector 112 receives the spectrum and converts the received spectrum into a plurality of digitized pixels, each digitized pixel having a known intensity of the light being received at each respective wavelength. The digitized data is sent to the CPU 114, whereby the CPU 114 preferably stores the intensity and wavelength values associated with each pixel in one or more look up tables. The CPU 114 also preferably stores the known reference values of each variable used in each equation. The CPU 114 then inserts the ambient spectral irradiance values as well as the blue light and retinal thermal hazard factors for each incremental wavelength in the wavelength range into equation (1). Thus, from the inserted values, the denominator value in equation (1) is determined.

Following, a substrate 104 or material 105 is measured by beaming the same light from the light source 102. For a substrate 104 that is transparent or translucent, the light is beamed through the substrate 104. However, for a material 105 that is opaque, the light is reflected off the surface of the material 105. In either embodiment, the light that is filtered by the substrate 104 or material 105 is a filtered, modified light which is eventually received at the Solid state diode array detector 120 as a spectrum representative of the modified light from the substrate 104 or material 105.

The solid state diode array detector 112 receives the modified spectrum and converts the received modified spectrum into digitized pixels, each digitized pixel having a known intensity of the modified, filtered light from the substrate 104 or material 105 at each respective wavelength. The digitized data is sent to the CPU 114, whereby the CPU 114 again stores the intensity and wavelength values associated with each pixel in one or more look up tables. The CPU 114 preferably compares, for each wavelength, the pixels of the modified light against the pixels already stored. The comparison of intensity between the pixels measured for the modified light and the pixels already stored determines the amount of wavelengths which are transmitted or reflected from the measured medium and thereby yields the filtered, transmission/reflection value T of the substrate 104 or material 105. The CPU 114 then inserts the filtered T value within the numerator coefficient of the equation (1) for each wavelength.

As stated above, the values of the ambient spectral irradiance values and blue light and retinal thermal hazard factors for each incremental wavelength in the wavelength range are already known and inserted into the numerator coefficient of equation (1). Following, the values in the numerator coefficient are summed for each wavelength in the range and the values in the denominator coefficient are summed for each wavelength in the range. Once the values are summed, the summed values in the numerator and the denominator are divided to determine the OPI exposure index. The OPI exposure index may also be subtracted from the whole value 1 to produce the protection index. In addition, either index value may be multiplied by 100 to yield a rounded number.

The advantage of the system and method of the present invention is that it is used to measure the material and calculate any desired integrated index to inform consumers of the protective properties of the material against harmful sunlight rays. The integrated index is used to quantify the ultra violet, infra-red, erythemal or aphakic exposure properties of the material. and provide an easy to communicate values within a range of values In addition, the integrated index is used to quantify the photopic and/or scotopic response capabilities of the material. Further, the integrated index is used to quantify the differential or mean color indices of the material in comparison to the color spectrum or another material. Moreover, the integrated index is used to quantify the heat flux absorbed by the material.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modification s may be made in the embodiment chosen for illustration without departing from the spirit and scope of the invention.

What is claimed is:

1. A method of calculating an integrated exposure index of a material for a desired wavelength range, the method comprising:
   measuring a filtered value of the material as a function of wavelength within the desired wavelength range; and
   calculating a protection index from the measured filtered value by mathematically combining the filtered values with a wavelength-specific biological hazard function.

2. The method according to claim 1 wherein calculating the protection index further comprises:
   summing a calculated denominator coefficient for each incremental wavelength within the desired wavelength range, thereby forming a summed denominator coefficient, wherein each denominator coefficient is calculated by combining an appropriate ambient spectral irradiance value with an appropriate hazard factor;
   summing a calculated numerator coefficient for each wavelength within the desired wavelength range, thereby forming a summed numerator coefficient, wherein the numerator coefficient is calculated by combining the appropriate ambient spectral irradiance value and the measured filtered value with the appropriate hazard factor; and
   dividing the summed numerator coefficient by the summed denominator coefficient, thereby forming a divided value.

3. The method according to claim 2 further comprising subtracting the divided value from a whole value, thereby generating a protection value.

4. The method according to claim 3 further comprising multiplying the protection value by a value of 100.

5. The method according to claim 2 wherein the protection index is a heat flux index, the heat flux index utilizing the hazard factor as an energy absorption factor within the wavelength range, the wavelength range having a minimum wavelength of 300 nanometers, the wavelength range having a maximum wavelength within a maximum range of 1000 nanometers and 12000 nanometers.

6. The method according to claim 2 wherein the protection index is an ocular protection index, the ocular protection index utilizing the hazard factor as a summation of a blue light hazard factor and a retinal thermal hazard factor for each wavelength within the wavelength range, the wavelength range having a minimum wavelength within a minimum range of 300 nanometers and 320 nanometers, the wavelength range having a maximum wavelength within a maximum range of 900 nanometers and 1400 nanometers.

7. The method according to claim 2 wherein the protection index is a UV protection index, the UV protection index utilizing the hazard factor as a blue light hazard factor within the wavelength range, the wavelength range having a minimum wavelength within a minimum range of 180 nanometers and 320 nanometers, the wavelength range having a maximum wavelength of 500 nanometers.

8. The method according to claim 2 wherein the protection index is a infra-red protection index, the infra-red protection index utilizing the hazard factor as a retinal thermal factor within the wavelength range, the wavelength range having a minimum wavelength within a minimum range of 300 nanometers and 385 nanometers, the wavelength range having a maximum wavelength within a maximum range of 900 nanometers and 5000 nanometers.

9. The method according to claim 3 wherein the protection index is an aphakic protection index, the aphakic index utilizing the hazard factor as an aphakic hazard factor within the wavelength range, the wavelength range having a minimum wavelength within a minimum range of 300 nanometers and 305 nanometers, the wavelength range having an approximate value of 700 nanometers.

10. The method according to claim 2 wherein the protection index is an erythemal protection index, the erythemal protection index utilizing the hazard factor as an erythemal response factor within the wavelength range, the wavelength range having a minimum wavelength range of 185 nanometers and 300 nanometers, the wavelength range having a maximum wavelength within a maximum range of 320 nanometers and 500 nanometers.

11. The method according to claim 1 wherein the filtered value is measured by transmitting light within the desired wavelength range through the material.

12. The method according to claim 1 wherein the filtered value is measured by reflecting light within the desired wavelength range off the material.

13. The method according to claim 11 wherein the material is a transparent material.

14. The method according to claim 11 wherein the material is a translucent material.

15. The method according to claim 12 wherein the material is an opaque material.

16. A method of quantifying a value representative of a responsiveness of a material for a desired wavelength range, the method comprising:
   measuring a filtered value of the material as a function of wavelength within the desired wavelength range; and
   calculating an integrated response index from the measured filtered values by mathematically combining the filtered values with a wavelength-specific response function.

17. The method according to claim 16 wherein calculating the integrated response index further comprises:
- summing a calculated denominator coefficient for each incremental wavelength within the desired wavelength range, thereby forming a summed denominator coefficient, wherein each denominator coefficient is calculated by combining a response function with an appropriate illumination source irradiance value;
- summing a calculated numerator coefficient for each wavelength within the desired wavelength range, thereby forming a summed numerator coefficient, wherein the numerator coefficient is calculated by combining the appropriate illumination source irradiance value and the response function with the measured filtered value; and
- dividing the summed numerator coefficient with the summed denominator coefficient, thereby forming a divided value.

18. The method according to claim 17 wherein the integrated response index is an integrated photopic response index, the integrated photopic response index utilizing the response function as an ocular photopic response function for each wavelength in the wavelength range, the wavelength range having a minimum wavelength of 400 nanometers, and the wavelength range having a maximum wavelength within a maximum range of 700 nanometers and 750 nanometers.

19. The method according to claim 17 wherein the integrated response index is an integrated scotopic response index, the integrated scotopic response index utilizing the response function as an ocular scotopic response function for each wavelength in the wavelength range, the wavelength range having a minimum wavelength of 400 nanometers, and the wavelength range having a maximum wavelength within a maximum range of 700 nanometers and 750 nanometers.

20. The method according to claim 17 wherein the integrated response index is an integrated photopic-scotopic response index, the integrated photopic-scotopic response index utilizing the response function as a summation of an ocular scotopic response function and an ocular photopic response function for each wavelength in the wavelength range, the wavelength range having a minimum wavelength of 400 nanometers, and the wavelength range having a maximum wavelength within a maximum range of 700 nanometers and 750 nanometers.

21. The method according to claim 16 wherein the filtered value is measured by transmitting light within the desired wavelength range through the material.

22. The method according to claim 16 wherein the filtered value is measured by reflecting light within the desired wavelength range off the material.

23. The method according to claim 21 wherein the material is a transparent material.

24. The method according to claim 21 wherein the material is a translucent material.

25. The method according to claim 22 wherein the material is an opaque material.

26. A method of calculating an integrated index of a material medium within a desired wavelength range, the method comprising:
- measuring a first spectrum value for each wavelength within the desired wavelength range;
- measuring a second spectrum value for each wavelength within the desired wavelength range; and
- calculating a differential color index from the measured first spectrum value and the measured second spectrum value by mathematically combining the measured first and second spectrum values with a wavelength-specific color response function.

27. The method according to claim 26 wherein calculating a differential color index further comprises:
- summing a calculated denominator coefficient for each incremental wavelength within the desired wavelength range, thereby forming a summed denominator coefficient, wherein each denominator coefficient is calculated by combining a illumination source irradiance value with an ocular photopic index factor and the measured second spectrum value;
- summing a calculated numerator coefficient for each wavelength within the desired wavelength range, thereby forming a summed numerator coefficient, wherein the numerator coefficient is calculated by combining the illumination source irradiance value with the ocular photopic index factor and a difference between the measured first and second spectrum values; and
- dividing the summed numerator coefficient by the summed denominator coefficient, thereby forming a divided value.

28. The method according to claim 26 wherein the wavelength range for the differential color index of a blue wavelength band includes a minimum wavelength of 400 nanometers and a maximum wavelength of 520 nanometers.

29. The method according to claim 26 wherein the wavelength range for the differential color index of a red wavelength band includes a minimum wavelength of 620 nanometers and a maximum wavelength of 700 nanometers.

30. The method according to claim 26 wherein the wavelength range for the differential color index of a yellow wavelength band includes a minimum wavelength of 520 nanometers and a maximum wavelength of 620 nanometers.

31. The method according to claim 26 wherein the first spectrum value is measured by transmitting light within the desired wavelength range through the material.

32. The method according to claim 26 wherein the first spectrum value is measured by reflecting light within the desired wavelength range off the material.

33. The method according to claim 31 wherein the material is a transparent material.

34. The method according to claim 31 wherein the material is a translucent material.

35. The method according to claim 32 wherein the material is an opaque material.

36. A method of calculating an integrated index of a material within a desired wavelength range, the method comprising:
- measuring a spectrum value of the material for each wavelength within the desired wavelength range; and
- calculating a mean color index from the measured spectrum value by mathematically combining the spectrum values with a wavelength-specific color response function.

37. The method according to claim 36 wherein calculating the mean color index further comprises the steps of:
- summing a plurality of numerator coefficients for each wavelength over the desired wavelength range, thereby forming a summed numerator coefficient, wherein each numerator coefficient combines the measured spectrum value with an illumination source irradiance value;
- summing a plurality of illumination source irradiance values for each wavelength within the desired wavelength range, thereby forming a summed illumination source irradiance value; and dividing the summed numerator coefficients by the summed illumination source irradiance value, thereby forming a divided value.

38. The method according to claim 36 wherein a minimum wavelength value in the wavelength range is 400 nanometers and a maximum wavelength value in the wavelength range has a maximum range between 700 nanometers and 750 nanometers.

39. The method according to claim 36 wherein the first spectrum value is measured by transmitting light within the desired wavelength range through the material.

40. The method according to claim 36 wherein the first spectrum value is measured by reflecting light within the desired wavelength range off the material.

41. The method according to claim 39 wherein the material is a transparent material.

42. The method according to claim 39 wherein the material is a translucent material.

43. The method according to claim 40 wherein the material is an opaque material.

44. An apparatus for calculating an integrated index value for a material comprising:
   one or more light sources for emitting light within a desired wavelength range to the material, thereby producing a modified light;
   a diffraction grating for diffracting the modified light at a predetermined angle as a modified spectrum;
   an array detector for detecting a first plurality of characteristics of the modified spectrum; and
   a controller coupled to the array detector, wherein the controller calculates the integrated index value of the material by comparing the plurality of characteristics of the modified spectrum with a second plurality of characteristics of a reference spectrum within the desired wavelength range.

45. An apparatus for calculating an integrated index value for a material comprising:
   means for emitting light within a desired wavelength range at the material, thereby producing a modified light;
   means for diffracting the modified light, thereby producing a modified spectrum;
   means for detecting the modified spectrum, wherein the spectrum detecting means detects a desired characteristic of the modified spectrum; and
   means for calculating the integrated index, the calculating means coupled to the spectrum detecting means, wherein the calculating means determines the integrated index value of the material by comparing the desired characteristic of the modified spectrum with a reference characteristic of a reference spectrum within the desired wavelength range.

46. An apparatus for calculating an integrated index value for a material comprising:
   a light source for emitting light within a desired wavelength range through the material, wherein the light passing through the material is a modified light;
   a grating device for producing a modified spectrum representative from the modified light;
   a detector assembly for detecting the modified spectrum, wherein the detector assembly detects a desired characteristic of the modified spectrum; and
   a circuit coupled to the detector assembly, the circuit for calculating the integrated index by comparing the desired characteristic with a corresponding characteristic of a reference spectrum within the desired wavelength range.

47. The apparatus according to claim 46 further comprising a conditioning apparatus for conditioning the light to include wavelengths only in the desired wavelength range.

48. The apparatus according to claim 47 wherein the conditioning apparatus is coupled to the detector assembly.

49. The apparatus according to claim 48 wherein the detector assembly further comprises:
   a spatial filter; and
   a solid state diode array detector.

50. The apparatus according to claim 47 wherein the conditioning apparatus is positioned between the light source and the material.

51. The apparatus according to claim 49 wherein the solid state diode array detector is a CCD array detector.

52. The apparatus according to claim 50 wherein the conditioning apparatus is a color balance filter.

53. The apparatus according to claim 52 wherein the light source further comprises a lamp and a plurality of light emitting diodes.

54. The apparatus according to claim 53 wherein the conditioning apparatus is a dichroic filter for combining light from the lamp and the plurality of light emitting diodes into a single emitted light.

55. The apparatus according to claim 53 wherein the conditioning apparatus is an integrating sphere for combining light from the lamp and the plurality of light emitting diodes into a single emitted light.

56. An apparatus for calculating an integrated index value for a material comprising:
   a light source for emitting light within a desired wavelength range at the material, wherein the light reflected off of the material is a modified light;
   a grating device for producing a modified spectrum representative of the modified light;
   a detector assembly for detecting the modified spectrum, wherein the detector assembly detects a desired characteristic of the modified spectrum; and
   a circuit coupled to the detector assembly, the circuit for calculating the integrated index by comparing the desired characteristic with a corresponding characteristic of a reference spectrum within the desired wavelength range.

57. The apparatus according to claim 56 further comprising a conditioning apparatus for conditioning the light to include wavelengths only in the desired wavelength range.

58. The apparatus according to claim 57 wherein the conditioning apparatus is coupled to the detector assembly.

59. The apparatus according to claim 57 wherein the detector assembly further comprises:
   a spatial filter; and
   a solid state diode array detector.

60. The apparatus according to claim 57 wherein the conditioning apparatus is positioned between the light source and the material.

61. The apparatus according to claim 57 wherein the solid state diode array detector is a CCD array detector.

62. The apparatus according to claim 57 wherein the conditioning apparatus is a color balance filter.

63. The apparatus according to claim 56 wherein the light source further comprises a lamp and a plurality of light emitting diodes.

64. The apparatus according to claim 62 wherein the conditioning apparatus is a dichroic filter for combining light from the lamp and the plurality of light emitting diodes into a single emitted light.

65. The apparatus according to claim 64 wherein the conditioning apparatus is an integrating sphere for combining light from the lamp and the plurality of light emitting diodes into a single emitted light.

* * * * *